United States Patent [19]

Ueda et al.

[11] Patent Number: 5,723,648

[45] Date of Patent: Mar. 3, 1998

[54] INTERMEDIATES FOR ANTI-MICROBIAL BENZOHETEROCYCLIC COMPOUNDS

[75] Inventors: Hiraki Ueda, Mishima; Hisashi Miyamoto; Hiroshi Yamashita, both of Tokushima; Hitoshi Tone, Itano, all of Japan

[73] Assignee: Otsuka Pharmaceutical Company, Limited, Tokyo-to, Japan

[21] Appl. No.: 676,034

[22] Filed: Jul. 5, 1996

Related U.S. Application Data

[62] Division of Ser. No. 179,239, Apr. 8, 1988, Pat. No. 5,563,138.

[30] Foreign Application Priority Data

| Apr. 16, 1987 | [JP] | Japan | 62-94198 |
| Apr. 24, 1987 | [JP] | Japan | 62-102351 |
| Apr. 30, 1987 | [JP] | Japan | 62-108361 |
| May 22, 1987 | [JP] | Japan | 62-126598 |
| Jun. 16, 1987 | [JP] | Japan | 62-149544 |
| Jul. 14, 1987 | [JP] | Japan | 62-176126 |
| Nov. 9, 1987 | [JP] | Japan | 62-283776 |
| Nov. 12, 1987 | [JP] | Japan | 62-287108 |

[51] Int. Cl.⁶ .......... C07C 229/34; C07C 69/66
[52] U.S. Cl. .......... 560/38; 560/53; 560/54; 549/68
[58] Field of Search .......... 560/38, 53, 54; 549/68

[56] References Cited

U.S. PATENT DOCUMENTS

| 4,578,473 | 3/1986 | Domagala et al. | 546/156 |
| 4,766,844 | 8/1988 | Grohe et al. | 118/288 |
| 4,920,120 | 4/1990 | Domagala et al. | 546/156 |
| 4,940,794 | 7/1990 | Hermeac et al. | 546/13 |
| 4,945,160 | 7/1990 | Kiely et al. | 546/156 |
| 4,980,470 | 12/1990 | Masuzawa et al. | 546/156 |

FOREIGN PATENT DOCUMENTS

| 899 399 | 7/1984 | Belgium . |
| 0 126 355 | 11/1984 | European Pat. Off. . |
| 0 178 388 | 4/1986 | European Pat. Off. . |
| 0 202 763 | 11/1986 | European Pat. Off. . |
| 0 206 101 | 12/1986 | European Pat. Off. . |
| 0 221 463 | 5/1987 | European Pat. Off. . |
| 0 230 053 | 7/1987 | European Pat. Off. . |
| 0 237 955 | 9/1987 | European Pat. Off. . |
| 0 242 789 | 10/1987 | European Pat. Off. . |
| 0 247 464 | 12/1987 | European Pat. Off. . |
| 0 306 764 | 3/1989 | European Pat. Off. . |
| 0 310 917 | 4/1989 | European Pat. Off. . |

OTHER PUBLICATIONS

Ueda, et al., "Chemical Abstracts," vol. 110, 1989, col. 110713109k.

Domagala, et al., "Chemical Abstracts," vol. 112, 1990, col. 112:98508a.

Matsumato, et al., "Chemical Abstracts," vol. 116, 1990, col. 112:172308d.

*Primary Examiner*—Bernard Dentz
*Attorney, Agent, or Firm*—Finnegan, Henderson, Farabow, Garrett & Dunner, L.L.P.

[57] ABSTRACT

Novel 4-oxoquinoline-3-carboxylic acid compounds of the formula:

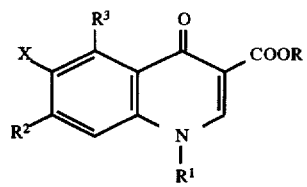

wherein $R^1$ is cyclopropyl which may have 1 to 3 substituents of alkyl and halogen; phenyl which may be substituted by 1 to 3 substituents of alkoxy, halogen and OH; alkyl which may be substituted by halogen, alkanoyloxy or OH; alkenyl; or thienyl. $R^2$ is 5- to 9-membered saturated or unsaturated heterocyclic ring which may be sustituted. $R^3$ is alkyl, R is H or alkyl, and X is halogen, and pharmaceutically acceptable salts thereof, said compounds having excellent antimicrobial activity and hence being useful as an antimicrobial agent, and a pharmaceutical composition containing said compound as an active ingredient.

5 Claims, No Drawings

INTERMEDIATES FOR ANTI-MICROBIAL BENZOHETEROCYCLIC COMPOUNDS

This application is a divisional of Ser. No. 07/179,239 filed Apr. 8, 1988 now U.S. Pat. No. 5,563,138.

The present invention relates to novel antimicrobial benzoheterocyclic compounds of the formula [1]:

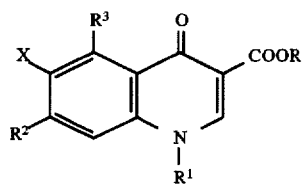

wherein $R^1$ is a cyclopropyl which may be substituted by 1 to 3 of substituents selected from the group consisting of a (lower) alkyl and a halogen atom, a phenyl which may be substituted by 1 to 3 of substituents selected from the group consisting of a (lower) alkoxy, a halogen atom and hydroxy on phenyl ring, a (lower) alkyl which may be substituted by a halogen atom, a (lower) alkanoyloxy or hydroxy, a (lower) alkenyl or thienyl, $R^2$ is a 5- to 9-membered saturated or unsaturated heterocyclic ring which may be substituted, $R^3$ is a (lower) alkyl, R is hydrogen atom or a (lower) alkyl, and X is a halogen atom, and pharmaceutically acceptable salts thereof.

The benzoheterocyclic compounds of the formula [1] and salts thereof have excellent antibacterial activities against various gram positive and gram negative bacteria, and are useful for the treatment of various infectious diseases induced by various bacteria in human, other animals and fish and are also useful as an external antimicrobial or disinfectant agent for medical instruments or the like.

PRIOR ART

There are many literatures which disclose 4-oxoquinoline-3-carboxylic acid derivaties useful as antibacterial agents. Among these literatures, European Patent Publication No. 178388 discloses 1-cyclopropyl-7-piperazino-dihydroquinoline carboxylic acid derivatives of the formula:

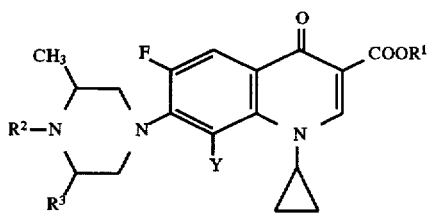

wherein $R^1$ is H or lower alkyl, $R^2$ is H, methyl, p-nitro(or amino)-benzyl, $R^3$ is H, methyl, or aminomethyl, and Y is Cl or F.

Japanese Patent First Publication (Kokai) No. 469/1987 discloses 1-cyclopropyl-dihydroquinoline carboxylic acid derivatives of the formula:

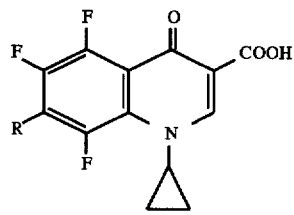

wherein R is substituted or unsubstituted pyrrolidinyl or piperazinyl.

WO 8606630 discloses 1-cycloalkyl-1,4-dihydro-4-oxoquinoline-3-carboxylic acid derivatives of the formula:

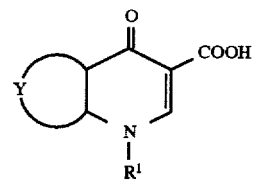

wherein $R^1$ is $C_3$–$C_6$ cycloalkyl, Y is optionally substituted 6-membered aromatic group.

U.S. Pat. No. 4,556,658 discloses 7-amino-1-cyclopropyl-3-quinoline carboxylic acid derivatives of the formula:

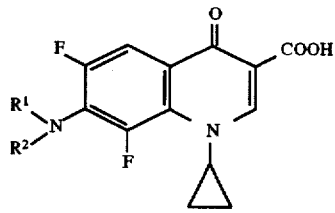

wherein $R^1$ and $R^2$ are each substituted or unsubstituted alkyl, or both may combine together with N atom to form a 5- or 6-membered heterocyclic ring.

Belgian Patent 899399 discloses 1-cyclopropyl-7-piperazinyl-dihydroquinoline carboxylic acid derivatives of the formula:

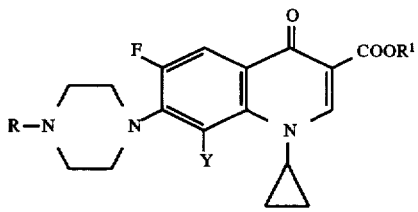

wherein R is H, methyl, or p-nitro(or amino)-benzyl, $R^1$ is H or lower alkyl, and Y is Cl, F, methyl.

Similar 1-substituted-7-heterocyclic group-substituted dihydroquinoline carboxylic acid derivatives are also disclosed in the literature.

However, these known literatures do not disclose any compound having an alkyl substituent at 5-position.

BRIEF DESCRIPTION OF THE INVENTION

The object of the present invention is to provide novel benzoheterocyclic compounds of the formula [1] and salts thereof which have excellent antimicrobial activity and excellent absorbability. Another object of the invention is to provide a pharmaceutical composition containing as an active ingredient a compound of the formula [1] or a pharmaceutically acceptable salt thereof, which is useful for the treatment of various infectious diseases. These and other objects of the invention will be apparent to persons skilled in the art from the following description.

DETAILED DESCRIPTION OF THE INVENTION

The novel benzoheterocyclic compounds of the present invention have the formula [1] as mentioned above and include pharmaceutically acceptable salts thereof.

In the specification, the term "a halogen atom" includes fluorine, chlorine, bromine or iodine atom.

The term "a cyclopropyl which may be substituted by 1 to 3 of substituents selected from the group consisting of a (lower) alkyl and a halogen atom" includes cyclopropyl which may be substituted by 1 to 3 of substituents selected from the group consisting of a straight chain or branched chain $C_1$–$C_6$ alkyl and a halogen atom, such as cyclopropyl, 2-fluoro-1-cyclopropyl, 2-chloro-1-cyclopropyl, 2-bromo-1-cyclopropyl, 2-iodo-1-cyclopropyl, 2,2-dichloro-1-cyclopropyl, 2,2-dibromo-1-cyclopropyl, 2,2,3-trichloro-1-cyclopropyl, 2-methyl-1-cyclopropyl, 2-ethyl-1-cyclopropyl, 2-propyl-1-cyclopropyl, 2-butyl-1-cyclopropyl, 2-pentyl-1-cyclopropyl, 2-hexyl-1-cyclopropyl, 2,2-dimethyl-1-cyclopropyl, 2,3-dimethyl-1-cyclopropyl, 2,2,3-trimethyl-1-cyctopropyl, 2-fluoro-3-methyl-1-cyclopropyl, 2,2-diethyl-1-cyclopropyl, 2-methyl-3-propyl-1-cyclopropyl, and the like.

The term "a (lower) alkyl" includes straight chain or branched chain $C_1$–$C_6$ alkyl, such as methyl, ethyl, propyl, isopropyl, butyl, tert-butyl, pentyl, hexyl, etc.

The term "a 5- to 9-membered saturated or unsaturated heterocyclic ring which may be substituted" denotes a 5- to 9-membered saturated or unsaturated heterocyclic ring which may be substituted by a (lower) alkyl; a cycloalkyl; a phenyl (lower) alkyl in which phenyl ring may be substituted by a lower alkoxy, nitro or amino; a phenyl which may be substituted by a halogen atom or a (lower) alkyl optionally substituted by 1 to 3 of halogen atoms; a pyridyl; a (lower) alkyl having 1 to 3 substituents selected from the group consisting of hydroxy, an amino which may be substituted by a (lower) alkyl, a (lower) alkanoyl, a cycloalkyl or a (lower) alkoxycarbonyl, a (lower) alkoxy and a halogen atom; a (lower) alkynyl; a (lower) alkanoyl which may be substituted by 1 to 7 of halogen atoms; a (lower) alkenylcarbonyl having 1 to 3 substituents selected from the group consisting of a halogen atom and a carboxy; a (lower) alkoxycarbonyl; an aminocarbonyl which may be substituted by a (lower) alkyl; a phenyl(lower)alkoxycarbonyl; an amino(lower)alkanoyl which may be substituted by a phenyl (lower)alkoxycarbonyl; a (lower) alkoxycarbonyl(lower) alkyl; a carboxy(lower)alkyl; an anilinocarbonyl(lower) alkyl; an amino which may be substituted by a (lower) alkyl, a phenyl(lower)alkyl, a (lower) alkoxycarbonyl or a (lower) alkanoyl; hydroxy; a (lower) alkylsulfonyl which may be substituted by 1 to 3 of halogen atoms; phthalide; a 2(5H)-furanone which may be substituted by 1 or 2 of halogen atoms; a sulfo(lower)alkyl; oxo; a (lower) alkoxy; a (lower) alkenyl; a halogen atom; a (lower) alkanoyloxy; a 2-oxo-1, 3-dioxolenemethyl which may be substituted by phenyl or a (lower) alkyl; a cycloalkylamino; a 2-oxo-1,3-dioxolenemethylamino which may be substituted by phenyl or a (lower) alkyl; a (lower) alkylthio; or thio, and includes more specifically 5- to 9-membered saturated or unsaturated heterocyclic rings which may be substituted by 1 to 3 of substituents selected from the group consisting of a straight chain or branched chain $C_1$–$C_6$ alkyl; a $C_3$–$C_8$ cycloalkyl; a phenylalkyl in which phenyl ring may be substituted by a straight chain or branched chain $C_1$–$C_6$ alkoxy, nitro or amino and the alkyl moiety is a straight chain or branched chain $C_1$–$C_6$ alkyl; a phenyl in which phenyl ring may be substituted by a halogen atom or by a straight chain or branched chain $C_1$–$C_6$ alkyl which may be substituted by 1 to 3 of halogen atoms; a pyridyl; an amino which may be substituted by 1 or 2 substituents selected from the group consisting of hydroxy, a straight chain or branched chain $C_1$–$C_6$ alkyl, a straight or branched chain $C_1$–$C_6$ alkanoyl, a $C_3$–$C_8$ cycloalkyl and a straight chain or branched chain ($C_1$–$C_6$)alkoxy-carbonyl; a straight chain or branched chain $C_1$–$C_6$ alkyl having 1 to 3 of substituents selected from the group consisting of a straight chain or branched chain $C_1$–$C_6$ alkoxy group and a halogen atom; a straight chain or branched chain $C_2$–$C_6$ alkynyl; a straight chain or branched chain $C_1$–$C_6$ alkanoyl which may be substituted by 1 to 7 of halogen atoms; a straight chain or branched chain ($C_2$–$C_6$) alkenyl-carbonyl substituted by 1 to 3 of halogen atoms or carboxy; a straight chain or branched chain ($C_1$–$C_6$)alkoxy-carbonyl; an aminocarbonyl which may be substituted by 1 or 2 of a straight chain or branched chain $C_1$–$C_6$ alkyl group; a phenylalkoxycarbonyl in which alkoxy moiety is a straight chain or branched chain $C_1$–$C_6$ alkoxy; a straight chain or branched chain $C_2$–$C_6$ aminoalkanoyl which may be substituted by a phenylalkoxycarbonyl in which alkoxy moiety is a straight chain or branched chain $C_1$–$C_6$ alkoxy; an alkoxycarbonylalkyl in which alkoxy and alkyl moieties are straight chain or branched chain $C_1$–$C_6$ alkoxy and alkyl, respectively; a carboxyalkyl in which alkyl moiety is a straight chain or branched chain $C_1$–$C_6$ alkyl; an anilinocarbonylalkyl in which alkyl moiety is a straight chain or branched chain $C_1$–$C_6$ alkyl; an amino which may be substituted by 1 or 2 of a straight chain or branched chain $C_1$–$C_6$ alkyl, a phenylalkyl in which alkyl moiety is a straight chain or branched chain $C_1$–$C_6$ alkyl, a straight chain or branched chain ($C_1$–$C_6$)alkoxy-carbonyl, or a straight chain or branched chain $C_1$–$C_6$ alkanoyl; hydroxy; a straight chain or branched chain $C_1$–$C_6$ alkylsulfonyl which may be substituted by 1 to 3 of halogen atoms; phthalide; a 2(5H)-furanone which may be substituted by 1 or 2 of halogen atoms; a sulfoalkyl in which alkyl moiety is a straight chain or branched chain $C_1$–$C_6$ alkyl; oxo; a straight chain or branched chain $C_1$–$C_6$ alkoxy; a straight chain or branched chain $C_2$–$C_6$ alkenyl; a halogen atom; a straight chain or branched chain $C_2$–$C_6$ alkanoyloxy; a $C_3$–$C_8$ cycloalkylamino; a straight chain or branched chain $C_1$–$C_6$ alkylthio; thio; a 2-oxo-1,3-dioxolenemethyl which may be substituted by phenyl or a straight chain or branched chain $C_1$–$C_6$alkyl; and a 2-oxo-1,3-dioxolenemethylamino which may be substituted by phenyl or a straight chain or branched chain $C_1$–$C_6$ alkyl , such as, for example, piperazinyl, piperidinyl, pyrrolidinyl, homopiperazinyl, morpholino, thiomorpholino, 1,2,5,6-tetrahydropyridyl, imidazolyl, 1,4-diazabicyclo-[4.3.0]nonan-4-yl, thiomorpholino-4-oxide, thiomorpholino-4,4-dioxide, pyrazolidinyl, hexahydropyridazinyl, pyridyl, thiazolidinyl, 2-thio-1-imidazolidinyl, 2-oxo-1-imidazolidinyl, 3,7-diazabicyclo[4.3.0]nonan-3-yl, 4-methyl-1-piperazinyl, 4-ethyl-1-piperazinyl, 4-propyl-1-piperazinyl, 4-t-butyl-1-piperazinyl, 4-pentyl-1-piperazinyl, 4-hexyl-1-piperazinyl, 3-methyl-1-piperazinyl, 3,4-dimethyl-1-piperazinyl, 2,5-dimethyl-1-piperazinyl, 2,4,5-trimethyl-1-piperazinyl, 3,4, 5-trimethyl-1-piperazinyl, 3-ethyl-1-piperazinyl, 3-propyl- 4-methyl-1-piperazinyl, 2-n-butyl-5-methyl-1-piperazinyl, 2-pentyl-5-hexyl-1-piperazinyl, 4-formyl-1-piperazinyl, 4-acetyl-1-piperazinyl, 4-propionyl-1-piperazinyl, 4-butyryl-1-piperazinyl, 4-pentanoyl-1-piperazinyl, 4-hexanoyl-1-piperazinyl, 4-($\alpha,\alpha,\alpha$-trifluoroacetyl)-1-piperazinyl, 4-($\beta,\beta,\beta$-trifluoro-$\alpha,\alpha$-difluoropropionyl)-1-piperazinyl, 4-($\gamma,\gamma,\gamma$-trifluoro-$\beta,\beta$-difluoro-$\alpha,\alpha$-difluorobutyryl)-1-piperazinyl, 4-($\alpha,\alpha$-dichloroacetyl)-1-piperazinyl, 4-($\alpha$-bromoacetyl)-1-piperazinyl, 4-($\alpha$-iodoacetyl)-1-piperazinyl, 4-(8-fluoropropionyl)-1-piperazinyl, 4-($\beta$-fluoro-$\alpha$-fluoropropionyl)-1-piperazinyl, 4-(6-fluorohexanoyl)-1-piperazinyl, 4-(4-chloropentanoyl)-1-piperazinyl, 4-benzyl-1-piperazinyl, 4-(2-phenylethyl)-1-piperazinyl, 4-(1-phenylethyl)-1-piperazinyl, 4-(3-phenylpropyl)-1-piperazinyl, 4-(4-phenylbutyl)-1-piperazinyl, 4-(1,1-dimethyl-2-phenylethyl)-1-piperazinyl, 4-(5-phenylpentyl)-1-piperazinyl, 4-(6-phenylhexyl)-1-piperazinyl, 4-(2-methyl-3-phenylpropyl)-1-piperazinyl, 4-amino-1-piperazinyl, 3-amino-1-piperazinyl, 2-amino-1-piperazinyl, 4-methylamino-1-piperazinyl, 3-dimethylamino-1-piperazinyl, 2-ethylamino-1-piperazinyl, 4-propylamino-1-piperazinyl, 4-t-butylamino-1-piperazinyl, 3-pentylamino-1-piperazinyl, 2-hexylamino-1-piperazinyl, 4-diethylamino-1-piperazinyl, 4-(N-methyl-N-n-butylamino)-1-piperazinyl, 3-(N-methyl-N-pentylamino)-1-piperazinyl, 2-(N-ethyl-N-hexylamino)-1-piperazinyl, 4-acetylamino-1-piperazinyl, 3-propylamino-1-piperazinyl, 2-propionylamino-1-piperazinyl, 4-butyrylamino-1-piperazinyl, 3-pentylamino-1-piperazinyl, 2-hexanoylamino-1-piperazinyl, 4-(N-methyl-N-acetylamino)-1-piperazinyl, 3-(N-ethyl-N-propionylamino)-1-piperazinyl, 4-hydroxy-1-piperazinyl, 3-hydroxy-1-piperazinyl, 2-hydroxy-1-piperazinyl, 4-methyl-sulfonyl-1-piperazinyl, 4-ethylsulfonyl-1-piperazinyl, 4-propylsulfonyl-1-piperazinyl, 4-n-butylsulfonyl-1-piperazinyl, 4-pentylsulfonyl-1-piperazinyl, 4-hexylsulfonyl-1-piperazinyl, 4-trifluoromethylsulfonyl-1-piperazinyl, 4-(2-fluoroethylsulfonyl)-1-piperazinyl, 4-(3-fluoropropylsulfonyl)-1-piperazinyl, 4-(4,4,4-trifluorobutylsulfonyl)-1-piperazinyl, 4-sulfonyl-1-piperazinyl, 4-(phthalid-3-yl)-1-piperazinyl, 4-(3,4-dibromo-2(5H)-furanon-5-yl)-1-piperazinyl, 4-(3,4-dichloro-2(5H)-furanon-5-yl)-1-piperazinyl, 4-( 2(5H)-furanon-5-yl)-1-piperazinyl, 4-(3-chloro-2(5H)-furanon-5-yl)-1-piperazinyl, 4-formyl-3-methyl-1-piperazinyl, 4-acetyl-3-ethyl-1-piperazinyl, 4-acetyl-2-methyl-1-piperazinyl, 4-methyl-3-hydroxymethyl-1-piperazinyl, 3-hydroxymethyl-1-piperazinyl, 4-ethyl-3-(2-hydroxyethyl)-1-piperazinyl, 3-(3-hydroxypropyl)-1-piperazinyl, 4-methyl-2-(4-hydroxybutyl)-1-piperazinyl, 4-ethyl-3-(5-hydroxypentyl)-1-piperazinyl, 3-(6-hydroxyhexyl)-1-piperazinyl, 4-(4-methoxybenzyl)-1-piperazinyl, 4-(3-ethoxybenzyl)-1-piperazinyl, 4-(2-propoxybenzyl)-1-piperazinyl, 4-(4-n-butoxybenzyl)-1-piperazinyl, 4-(3-pentyloxybenzyl)-1-piperazinyl, 4-(2-hexyloxybenzyl)-1-piperazinyl, 4-(4-nitrobenzyl)-1-piperazinyl, 4-(3-nitrobenzyl)-1-piperazinyl, 4-(4-aminobenzyl)-1-piperazinyl, 4-(2-aminobenzyl)-1-piperazinyl, 4-cyclopropyl-1-piperazinyl, 4-cyclobutyl-1-piperazinyl, 4-cyclopentyl-1-piperazinyl, 4-cyclohexyl-1-piperazinyl, 4-cycloheptyl-1-piperazinyl, 4-cyclooctyl-1-piperazinyl, 4-phenyl-1-piperazinyl, 4-(4-fluorophenyl)-1-piperazinyl, 4-(3-bromophenyl)-1-piperazinyl, 4-(2-chlorophenyl)-1-piperazinyl, 4-(4-iodophenyl)-1-piperazinyl, 4-(4-methylphenyl)-1-piperazinyl, 4-(3-ethylphenyl)-1-piperazinyl, 4-(2-propylphenyl)-1-piperazinyl, 4-(4-n-butylphenyl)-1-piperazinyl, 4-(3-pentylphenyl)-1-piperazinyl, 4-(2-hexylphenyl)-1-piperazinyl, 4-(4-trifluoromethylphenyl)-1-piperazinyl, 4-[3-(2-chloroethyl)phenyl]-1-piperazinyl, 4-[2-(3,3-dibromopropyl)phenyl]-1-piperazinyl, 4-[4-(4-chlorobutyl)phenyl]-1-piperazinyl, 4-hydroxymethyl-1-piperazinyl, 4-(2-hydroxyethyl)-1-piperazinyl, 4-(3-hydroxypropyl)-1-piperazinyl, 4-(3-chloropropyl)-1-piperazinyl, 4-(bromomethyl)-1-piperazinyl, 4-(2-fluoroethyl)-1-piperazinyl, 4-(4-chlorobutyl)-1-piperazinyl, 4-(3-fluoropentyl)-1-piperazinyl, 4-(2,3-dichlorohexyl)-1-piperazinyl, 4-(2,2,2-trifluoroethyl)-1-piperazinyl, 4-(trifluoromethyl)-1-piperazinyl, 4-aminomethyl-1-piperazinyl, 4-(3-dimethylaminopropyl)-1-piperazinyl, 4-(2-ethylaminoethyl)-1-piperazinyl, 4-(4-propylaminobutyl)-1-piperazinyl, 4-(5-n-butylaminopentyl)-1-piperazinyl, 4-(6-pentylaminohexyl)-1-piperazinyl, 4-(N-methyl-N-ethylaminomethyl)-1-piperazinyl, 4-(N-methyl-N-propylaminomethyl)-1-piperazinyl, 4-(2-diethylaminoethyl)-1-piperazinyl, 4-(methoxymethyl)-1-piperazinyl, 4-(ethoxymethyl)-1-piperazinyl, 4-(2-propoxyethyl)-1-piperazinyl, 4-(3-butoxypropyl)-1-piperazinyl, 4-(4-pentyloxybutyl)-1-piperazinyl, 4-(5-hexyloxypentyl)-1-piperazinyl, 4-(6-methoxyhexyl)-1-piperazinyl, 4-propargyl-1-piperazinyl, 4-(2-butynyl)-1-piperazinyl, 4-(3-butynyl)-1-piperazinyl, 4-(1-methyl-2-propynyl)-1-piperazinyl, 4-(2-pentynyl)-1-piperazinyl, 4-(2-hexynyl)-1-piperazinyl, 4-ethynyl-1-piperazinyl, 4-vinyl-1-piperazinyl, 4-allyl-1-piperazinyl, 4-(2-butenyl)-1-piperazinyl, 4-(3-butenyl)-1-piperazinyl, 4-(1-methylallyl)-1-piperazinyl, 4-(2-pentenyl)-1-piperazinyl, 4-(2-hexenyl)-1-piperazinyl, 2-oxo-1-piperazinyl, 3-oxo-1-piperazinyl, 4-oxo-3-methyl-1-piperazinyl, 4,4-dimethyl-1-piperazinyl, 4-(2-pyridyl)-1-piperazinyl, 4-(3-pyridyl)-1-piperazinyl, 4-(4-pyridyl)-1-piperazinyl, 4-carbamoyl-1-piperazinyl, 4-dimethylaminocarbonyl-1-piperazinyl, 4-ethylaminocarbonyl-1-piperazinyl, 4-propylaminocarbonyl-1-piperazinyl, 4-butylaminocarbonyl-1-piperazinyl, 4-pentylaminocarbonyl-1-piperazinyl, 4-hexylaminocarbonyl-1-piperazinyl, 4-diethylaminocarbonyl-1-piperazinyl, 4-(N-methyl-N-propylaminocarbonyl)-1-piperazinyl, 4-methoxycarbonyl-1-piperazinyl, 4-ethoxycarbonyl-1-piperazinyl, 4-propoxycarbonyl-1-piperazinyl, 4-tert-butoxycarbonyl-1-piperazinyl, 4-pentyloxycarbonyl-1-piperazinyl, 4-hexyloxycarbonyl-1-piperazinyl, 4-benzyloxycarbonyl-1-piperazinyl, 4-(2-phenylethoxycarbonyl)-1-piperazinyl, 4-(3-phenylpropoxycarbonyl)-1-piperazinyl, 4-(4-phenylbutoxycarbonyl)-1-piperazinyl, 4-(5-phenylpentyloxycarbonyl)-1-piperazinyl, 4-(6-phenylhexyloxycarbonyl)-1-piperazinyl, 4-(2-aminoacetyl)-1-piperazinyl, 4-(3-aminopropionyl)-1-piperazinyl, 4-(4-aminobutyryl)-1-piperazinyl, 4-(5-aminopentanoyl)-1-piperazinyl, 4-(6-aminohexanoyl)-1-piperazinyl, 4-(2-benzyloxycarbonylaminoacetyl)-1-piperazinyl, 4-[2-(2-phenylethoxycarbonylamino)acetyl]-1-piperazinyl, 4-[2-(3-phenylpropoxycarbonylamino)acetyl]-1-piperazinyl, 4-[2-(4-phenylbutoxycarbonylamino)acetyl]-1-piperazinyl, 4-methoxycarbonylmethyl-1-piperazinyl, 4-ethoxycarbonylmethyl-1-piperazinyl, 4-(2-ethoxycarbonylethyl)-1-piperazinyl, 4-(3-propoxycarbonylpropyl)-1-piperazinyl, 4-(4-butoxycarbonylbutyl)-1-piperazinyl, 4-(5-pentyloxycarbonylpentyl)-1-piperazinyl, 4-(6-hexyloxycarbonylhexyl)-1-piperazinyl, 4-carbonylmethyl-1-piperazinyl, 4-(2-carboxyethyl)-1-piperazinyl, 4-(3-carboxypropyl)-1-piperazinyl, 4-(4-carboxybutyl)-1- piperazinyl, 4-(5-carboxypentyl)-1-piperazinyl, 4-(6-carboxyhexyl)-1-piperazinyl, 4-(anilinocarbonylmethyl)-1-piperazinyl, 4-(2-anilinocarbonylethyl)-1-piperazinyl, 4-(3-anilinocarbonylpropyl)-1-piperazinyl, 4-(4-anilinocarbonylbutyl)-1-piperazinyl, 4-(5-anilinocarbonylpentyl)-1-piperazinyl, 4-(6-anilinocarbonylhexyl)-1-piperazinyl, 4-(3-carboxyacryloyl)-1-piperazinyl, 4-(3-carboxy-2,3-dichloroacryloyl)-1-piperazinyl, 4-methyl-1-piperidinyl, 4-ethyl-1-piperidinyl, 4-propyl-1-piperidinyl, 4-n-butyl-1-piperidinyl,.4-pentyl-1-piperidinyl, 4-hexyl-1-piperidinyl, 4-methoxy-1-piperidinyl, 4-ethoxy-1-piperidinyl, 4-propoxy-1-piperidinyl, 4-n-butoxy-1-piperidinyl, 4-pentyloxy-1-piperidinyl, 4-hexyloxy-1-piperidinyl, 4-acetyloxy-1-piperidinyl, 4-propionyloxy-1-piperidinyl, 4-butyryloxy-1-piperidinyl, 4-pentanoyloxy-1-piperidinyl, 4-hexanoyloxy-1-piperidinyl, 4-methoxycarbonyloxy-1-piperidinyl, 4-ethoxycarbonyl-1-piperidinyl, 4-propoxycarbonyl-1-piperidinyl, 4-n-butoxycarbonyl-1-piperidinyl, 4-pentyloxycarbonyl-1-piperidinyl, 4-hexyloxycarbonyl-1-piperidinyl, 4-benzyl-1-piperidinyl, 4-(2-phenylethyl)-1-piperidinyl, 4-(1-phenylethyl)-1-piperidinyl, 4-(3-phenylpropyl)-1-piperidinyl, 4-(4-phenylbutyl)-1-piperidinyl, 4-(5-phenylpentyl)-1-piperidinyl, 4-(6-phenylhexyl)-1-piperidinyl, 4-hydroxy-1-piperidinyl, 3-hydroxy-1-piperidinyl, 2-hydroxy-1-piperidinyl, 4-amino-1-piperidinyl, 3-amino-1-piperidinyl, 2-amino-1-piperidinyl, 4-dimethylamino-1-piperidinyl, 4-methylamino-1-piperidinyl, 3-ethylamino-1-piperidinyl, 4-methylamino-1-piperidinyl, 4-n-butylamino-1-piperidinyl, 2-propylamino-1-piperidinyl, 4-n-butylamino-1-piperidinyl, 3-pentylamino-1-piperidinyl, 4-hexylamino-1-piperidinyl, 3-diethylamino-1-piperidinyl, 4-(N-methyl-N-propylamino)-1-piperidinyl, 4-carbamoyl-1-piperidinyl, 3-carbamoyl-1-piperidinyl, 3,5-dimethyl-1-piperidinyl, 2,5-dimethyl-1-piperidinyl, 4-oxo-1-piperidinyl, 3-oxo-1-piperidinyl, 3-hydroxy-1-pyrrolidinyl, 3-amino-1-pyrrolidinyl, 2-hydroxy-1-pyrrolidinyl, 2-amino-1-pyrrolidinyl, 3-methylamino-1-pyrrolidinyl, 3-dimethylamino-1-pyrrolidinyl, 2-ethylamino-1-pyrrolidinyl, 3-propylamino-1-pyrrolidinyl, 2-n-butylamino-1-pyrrolidinyl, 3-pentylamino-1-pyrrolidinyl, 2-hexylamino-1-pyrrolidinyl, 3-diethylamino-1-pyrrolidinyl, 3-(N-methyl-N-propylamino)-1-pyrrolidinyl, 2-(N-ethyl-N-n-butylamino)-1-pyrrolidinyl, 3-acetylamino-1-pyrrolidinyl, 3-propionylamino-1-pyrrolidinyl, 2-butyrylamino-1-pyrrolidinyl, 3-pentanoylamino-1-pyrrolidinyl, 2-hexanoylamino-1-pyrrolidinyl, 3-hydroxymethyl-1-pyrrolidinyl, 2-(2-hydroxyethyl)-1-pyrrolidinyl, 3-(3-hydroxypropyl)-1-pyrrolidinyl, 2-(4-hydroxybutyl)-1-pyrrolidinyl, 3-(5-hydroxypentyl)-1-pyrrolidinyl, 3-(6-hydroxyhexyl)-1-pyrrolidinyl, 3-aminomethyl-1-pyrrolidinyl, 3-(2-aminoethyl)-1-pyrrolidinyl, 2-(3-aminopropyl)-1-pyrrolidinyl, 3-(4-aminobutyl)-1-pyrrolidinyl, 3-(5-aminopentyl)-1-pyrrolidinyl, 3-(6-aminohexyl)-1-pyrrolidinyl, 3-(methylaminomethyl)-1-pyrrolidinyl, 3-(2-ethylaminoethyl)-1-pyrrolidinyl, 3-(3-propylaminopropyl)-1-pyrrolidinyl, 2-(4-n-butylaminobutyl)-1-pyrrolidinyl, 3-(5-pentylaminopentyl)-1-pyrrolidinyl, 3-(6-hexylaminohexyl)-1-pyrrolidinyl, 3-(dimethylaminomethyl)-1-pyrrolidinyl, 2-(N-methyl-N-ethylaminomethyl)-1-pyrrolidinyl, 3-(N-ethyl-N-n-butylaminomethyl)-1-pyrrolidinyl, 3-methylaminomethyl-4-methyl-1-pyrrolidinyl, 3-methylaminomethyl-4-fluoro-1-pyrrolidinyl, 3-methylamino-4-methyl-1-pyrrolidinyl, 3-methylamino-4-chloro-1-pyrrolidinyl, 3-methylaminomethyl-4-chloro-1-pyrrolidinyl, 3-methylamino-4-fluoro-1-pyrrolidinyl, 3-ethylaminomethyl-4-ethyl-1-pyrrolidinyl, 4-propylaminomethyl-2-propyl-1-pyrrolidinyl, 4-n-butylaminomethyl-2-fluoro-1-pyrrolidinyl, 4-pentylaminomethyl-2-n-butyl-1-pyrrolidinyl, 4-hexylaminomethyl-2-chloro-1-pyrrolidinyl, 4-propylamino-2-chloro-1-pyrrolidinyl, 4-n-butylamino-2-hexyl-1-pyrrolidinyl, 3-pentylamino-4-ethyl-1-pyrrolidinyl, 3-hexylamino-4-fluoro-1-pyrrolidinyl, 4-methyl-1-homopiperazinyl, 4-ethyl-1-homopiperazinyl, 4-propyl-1-homopiperazinyl, 4-n-butyl-1-homopiperazinyl, 4-pentyl-1-homopiperazinyl, 4-hexyl-1-homopiperazinyl, 4-formyl-1-homopiperazinyl, 4-acetyl-1-homopiperazinyl, 4-propionyl-1-homopiperazinyl, 4-butyryl-1-homopiperazinyl, pentanoyl-1-homopiperazinyl, 4-hexanoyl-1-homopiperazinyl, 2-methyl-1-hexahydropyridazyl, 2-ethyl-1-hexahydropyridazyl, 2-propyl-1-hexahydropyridazyl, 2-n-butyl-1-hexahydropyridazyl, 2-pentyl-1-hexahydropyridazyl, 2-hexyl-1-hexahydropyridazyl, 2-formyl-1-hexahydropyridazyl, 2-acetyl-1-hexahydropyridazyl, 2-propionyl-1-hexahydropyridazyl, 2-butyryl-1-hexahydropyridazyl, 2-pentanoyl-1-hexahydropyridazyl, 2-hexanoyl-1-hexahydropyridazyl, 2-methyl-1-pyrazolidinyl, 2-ethyl-1-pyrazolidinyl, 2-propyl-1-pyrazolidinyl, 2-n-butyl-1-pyrazolidinyl, 2-pentyl-1-pyrazolidinyl, 2-hexyl-1-pyrazolidinyl, 2-formyl-1-pyrazolidinyl, 2-acetyl-1-pyrazolidinyl, 2-propionyl-1-pyrazolidinyl, 2-butyryl-1-pyrazolidinyl, 2-pentanoyl-1-pyrazolidinyl, 2-hexanoyl-1-pyrazolidinyl, 3,5-dimethylmorpholino, 3-methylmorpholino, 3-ethylmorpholino, 2-propylmorpholino, 3-n-butylmorpholino, 3-pentyl-5-methylmorpholino, 3-hexyl-5-ethylmorpholino, 3-aminomethylmorpholino, 3-methylaminomethylmorpholino, 2-ethylaminomethylmorpholino, 3-propylaminomethylmorpholino, 3-n-butylaminomethylmorpholino, 2-pentylaminomethylmorpholino, 3-hexylaminomethylmorpholino, 3-(2-methylaminoethyl)morpholino, 3-(3-methylaminopropyl)morpholino, 3-(4-methylaminobutyl)morpholino, 2-(5-methylaminopentyl)morpholino, 3-(6-methylaminohexyl)morpholino, 4-(5-methyl-2-oxo-1,3-dioxolen-4-yl)methyl-1-piperazinyl, 4-(5-tert-butyl-2-oxo-1,3-dioxolen-4-yl)methyl-1-piperazinyl, 4-(5-phenyl-2-oxo-1,3-dioxolen-4-yl)methyl-1-piperazinyl, 4-(2-oxo-1,3-dioxolen-4-yl)methyl-1-piperazinyl, 3-(5-methyl-2-oxo-1,3-dioxolen-4-yl)methylamino-1-pyrrolidinyl, 4-(5-methyl-2-oxo-1,3-dioxolen-4-yl)methylamino-1-piperidinyl, 3-(5-phenyl-2-oxo-1,3-dioxolen-4-yl)methylaminomorpholino, 3,5-dimethyl-1-piperazinyl, 3,3-dimethyl-1-piperazinyl, 4-acetyl-3-methyl-1-piperazinyl, 3-ethyl-1-piperazinyl, 3-ethyl-4-methyl-1-piperazinyl, 3-trifluoromethyl-1-piperazinyl, 3-(fluoromethyl)-1-piperazinyl, 3-methylthio-1-piperazinyl, 4-methylthio-1-piperazinyl, 3-ethylthio-1-piperazinyl, 3-methylthiomorpholino, 4-fluoro-1-piperidinyl, 3-fluoro-1-piperazinyl, 3-chloro-1-piperazinyl, 3-amino-4-fluoro-1-pyrrolidinyl, 3-amino-4-hydroxy-1-pyrrolidinyl, 3-amino-4-methoxy-1-pyrrolidinyl, 3-amino-4-fluoro-1-piperidinyl, 3-amino-4-hydroxy-1-piperidinyl, 3-amino-4-methyl-1-pyrrolidinyl, 4-benzyl-3-methyl-1-piperazinyl, 3-fluoromethylmorpholino, 3-chloromethylmorpholino, 4-oxo-1-piperidinyl, 3-oxo-1-piperidinyl, 2-oxo-1-piperidinyl, 3-acetylaminomethyl-1-pyrrolidinyl, 3-(N-ethyl-N-acetylamino)-methyl-1-pyrrolidinyl, 3-t-butoxycarbonylaminomethyl-1-pyrrolidinyl, 3-ethylaminomethyl-1-pyrrolidinyl, 4-cyclopropylamino-1-piperazinyl, 3-cyclopropylamino-1- pyrrolidinyl, 4-cyclopentylamino-1-piperazinyl, 4-cyclohexylamino-1-piperazinyl, 3-cycloheptylamino-1-pyrrolidinyl, 4-cyclooctylamino-1-piperidinyl, 4-cyclopropylamino-1-piperidinyl, 3-cyclopropylaminomorpholino, 4-thio-1-piperidinyl, 3-thio-1-piperazinyl, 3-thiomorpholino, 4-cyclopropylaminomethyl-1-piperazinyl, 3-cyclopropylaminomethyl-1-pyrrolidinyl, 4-cyclopropylaminomethyl-1-piperidinyl, 3-cyclopropylaminomethylmorpholino, 4-(2-cyclopentylaminoethyl)-1-piperazinyl, 4-(3-cyclohexylaminopropyl)-1-piperazinyl, 3-(4-cyclobutylaminobutyl)-1-pyrrolidinyl, 4-(5-cyclooctylaminopentyl)-1-piperidinyl, 4-(6-cyclopropylaminohexyl)morpholino, 3-acetylaminomethyl-1-pyrrolidinyl, 4-(2-propionylaminoethyl)-1-piperazinyl, 4-(3-butyrylaminopropyl)-1-piperidinyl, 3-(4-pentanoylaminobutyl)morpholino, 4-(5-hexanoylaminopentyl)-1-piperazinyl, 3-(6-acetylaminohexyl)-1-pyrrolidinyl, 4-(N-acetyl-N-ethylamino)methyl-1-piperazinyl, 4-(N-cyclopropyl-N-acetylamino)methyl-1-pyrrolidinyl, 4-(methoxycarbonylaminomethyl)-1-piperazinyl, 4-(2-ethoxycarbonylaminoethyl)-1-piperidinyl, 3-(3-propoxycarbonylaminopropyl)morpholino, 3-(4-pentyloxycarbonylaminobutyl)-1-pyrrolidinyl, 3-(5-hexyloxycarbonylaminopentyl)-1-pyrrolidinyl, 4-(6-t-butoxycarbonylaminohexyl)-1-piperazinyl, 3-(N-t-butoxycarbonyl-N-ethylaminomethyl)-1-pyrrolidinyl, 3-(N-t-butoxycarbonyl-N-methylaminomethyl)-1-pyrrolidinyl, 3-(N-t-butoxycarbonyl-N-cyclopropylaminomethyl)-1-pyrrolidinyl, 4-(N-methoxy-carbonyl-N-cyclopropylaminomethyl)-1-piperazinyl and 4-(N-propoxycarbonyl-N-cyclohexylaminomethyl)-1-piperidinyl. The term "a 5- to 9-membered saturated or unsaturated heterocyclic ring which may be substituted" also includes the group represented by the formula:

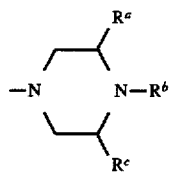

wherein $R^a$ is hydrogen atom or a (lower) alkyl, $R^b$ is hydrogen atom, a (lower) alkyl, a (lower) alkanoyl, a phenyl (lower)alkyl, or a 2-oxo-1,3-dioxolenemethyl which is substituted by a (lower) alkyl, and $R^c$ is hydrogen atom or a (lower) alkyl; the group represented by the formula:

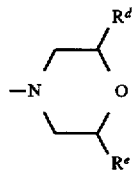

wherein $R^d$ is hydrogen atom or a (lower) alkyl, and $R^e$ is hydrogen atom or a (lower) alkyl; the group represented by the formula:

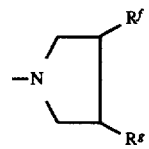

wherein $R^f$ is an amino which may be substituted by 1 or 2 substituents selected from the group consisting of a (lower) alkyl and a (lower) alkoxycarbonyl, or a amino(lower)alkyl which may be substituted by 1 or 2 substituents selected from the group consisting of a (lower) alkyl and a (lower) alkoxycarbonyl, $R^g$ is hydrogen atom or a (lower) alkyl; the group represented by the formula:

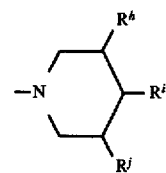

wherein $R^h$ is hydrogen atom or a (lower) alkyl, $R^i$ is hydrogen atom, hydroxy, a halogen atom or oxo, and $R^j$ is hydrogen atom or a (lower) alkly; and the like.

The term "a cycloalkyl" includes $C_3$–$C_8$ cycloalkyl such as cyclopropyl, cyclobutyl, cyclopentyl, cyclohexyl, cycloheptyl or cyclooctyl.

The term "a phenyl (lower) alkyl in which phenyl ring may be substituted by a (lower) alkoxy, nitro or amino" includes phenylalkyl in which phenyl ring may be substituted by a straight chain or branched chain $C_1$–$C_6$ alkoxy, nitro or amino and the alkyl moiety is a straight chain or branched chain $C_1$–$C_6$ alkyl, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 4-methoxybenzyl, 3-ethoxybenzyl, 2-propoxybenzyl, 4-n-butoxybenzyl, 3-pentyloxybenzyl, 2-hexyloxybenzyl, 4-nitrobenzyl, 3-nitrobenzyl, 4-aminobenzyl, 2-aminobenzyl, 2-(4-methoxyphenyl)ethyl, 1-(3-ethoxyphenyl)ethyl, 3-(2-propoxyphenyl)propyl, 4-(4-n-butoxyphenyl)butyl, 5-(2-nitrophenyl)pentyl or 6-(3-aminophenyl)hexyl.

The term "a phenyl which may be substituted by a halogen atom or a (lower) alkyl which may be substituted by 1 to 3 of halogen atoms" includes phenyl in which phenyl ring may be substituted by a halogen atom or by a straight chain or branched chain $C_1$–$C_6$ alkyl which may be substituted by 1 to 3 of halogen atoms, such as phenyl, 4-fluorophenyl, 3-bromophenyl, 2-chlorophenyl, 4-iodophenyl, 4-methylphenyl, 3-ethylphenyl, 2-propylphenyl, 4-n-butylphenyl, 3-pentylphenyl, 2-hexylphenyl, 4-trifluoromethylphenyl, 3-(2-chloroethyl) phenyl, 2-(3,3-dibromopropyl)phenyl, 4-(4-chlorobutyl)phenyl, 3-(5-iodopentyl)phenyl, 4-(6-fluorohexyl)phenyl, 2-(1,2,2-trifluoroethyl)phenyl or 4-(2,2,2- trifluoroethyl) phenyl.

The term "a (lower) alkyl having 1 to 3 of substituents selected from the group consisting of hydroxy, an amino which may be substituted by a (lower) alkyl, a (lower) alkanoyl, a cycloalkyl or a (lower) alkoxycarbonyl, a (lower) alkoxy and a halogen atom" includes a straight chain or branched chain $C_1$–$C_6$ alkyl having 1 to 3 of substituents selected from the group consisting of hydroxy; an amino which may be substituted by 1 or 2 substituents selected from the group consisting of a straight chain or branched chain $C_1$–$C_6$ alkyl, a straight chain or branched chain $C_1$–$C_6$ alkanoyl, a $C_3$–$C_8$ cycloalkyl and a straight chain or branched chain ($C_1$–$C_6$)alkoxy-carbonyl; a straight chain or branched chain $C_1$–$C_6$ alkoxy and a halogen atom, such as hyroxymethyl, 2-hydroxyethyl, 1-hyroxyethyl, 3-hydroxypropyl, 4-hydroxybutyl, 5-hyroxypentyl, 6-hydroxyhexyl, 3-chloropropyl, bromomethyl, 2-fluoroethyl, 4-chlorobutyl, 3-fluoropentyl, 2,3-dichlorohexyl, 2,2,2-trifluoroethyl, trifluoromethyl, aminomethyl, 2-aminoethyl, 1-aminoethyl, 3-aminopropyl, 4-aminobutyl, 5-aminopentyl, 6-aminohexyl, 3-dimethylaminopropyl, 2-ethylaminoethyl, 4-propylaminobutyl, 5-n-butylaminopentyl, 6-pentylaminohexyl, methylaminomethyl, diethylaminomethyl, 2-dipropylaminoethyl, 1-di-n-butylaminoethyl, 3-dipentylaminopropyl, 4-dihexylaminobutyl, N-methyl-N-ethylaminomethyl, N-methyl-N-propylaminomethyl, methoxymethyl, ethoxymethyl, 2-propoxyethyl, 3-butoxypropyl, 4-pentyloxybutyl, 5-hexyloxypentyl, 6-methoxyhexyl, propoxymetyl, 1-ethoxyethyl, 2-hexyloxyethyl, formylaminomethyl, acetylaminomethyl, 2-propanoylaminoethyl, 3-butyrylaminopropyl, 4-pentanoylaminobutyl, 5-hexanoylaminopentyl, 6-acetylaminohexyl, propanoylaminomethyl, 1-acetylaminoethyl, 2-hexanoylaminoethyl, N-acetyl-N-methylaminomethyl, N-acetyl-N-ethylaminomethyl, N-acetyl-N-cyclopropylaminomethyl, N,N-dicyclopropylaminomethyl, cyclopropylaminomethyl, 2-cyclobutylaminoethyl, 3-cyclopentylaminopropyl, 1-cyclopropylaminoethyl, 2-cyclopropylaminoethyl, aminopropyl, 4-cyclohexylaminobutyl, 5-cycloheptylaminopentyl, 6-cyclooctylaminohexyl, N-methyl-N-cyclopropylaminomethyl, N-ethyl-N-cyclopropylaminomethyl, methoxycarbonylaminomethyl, 2-ethoxycarbonylaminoethyl, 3-propoxycarbonylaminopropyl, 4-t-butoxycarbonylaminobutyl, 5-pentyloxycarbonylaminopentyl, 6-hexyloxycarbonylaminohexyl, t-butoxycarbonylaminomethyl, 2-t-butoxycarbonylaminoethyl, 1-t-butoxycarbonylaminoethyl, N-t-butoxycarbonyl-N-methylaminomethyl, N-t-butoxycarbonyl-N-ethylaminomethyl or N-t-butoxycarbonyl-N-cyclopropylaminomethyl.

The term "a (lower) alkanoyl which may be substituted by 1 to 7 of halogen atoms" includes a straight chain or branched chain $C_1$–$C_6$ alkanoyl which may be substituted by 1 to 7 of halogen atoms, such as formyl, acetyl, propionyl, butyryl, pentanoyl, hexanoyl, α,α,α-trifluoroacetyl, β,β,β-trifluoro-α,α-difluoropropionyl, γ,γ,γ-trifluoro-β,β-difluoro-α,α-difluorobutyryl, α,α-dichloroacetyl, α-bromoacetyl, α-iodoacetyl, β-fluoropropionyl, β-fluoro-α-fluoropropionyl, 6-fluorohexanoyl or 4-chloropentanoyl, 3,3,3-trifluoropropionyl.

The term "a (lower) alkenylcarbonyl having 1 to 3 substituents selected from the group consisting of a halogen atom and a carboxy" includes a straight chain or branched chain ($C_2$–$C_6$)alkenyl-carbonyl having 1 to 3 of substituents selected from the group consisting of a halogen atom and a carboxy, such as 3-carboxyacryloyl, 3-carboxy-2,3-dichloroacryloyl, 3-carboxy-2,3-dibromoacryloyl, 4-carboxycrotonoyl, 4-carboxyisocrotonoyl, 5-carboxy-3-pentenoyl, 6-carboxy-4-hexenoyl, 4-carboxy-3-fluorocrotonoyl or 5-carboxy-3,4-dichloro-3-hexenoyl.

The term "a (lower) alkoxycarbonyl" includes a straight chain or branched chain ($C_1$–$C_6$)alkoxy-carbonyl, such as methoxycarbonyl, ethoxycarbonyl, propoxycarbonyl, isopropoxycarbonyl, butoxycarbonyl, tert-butoxycarbonyl, pentyloxycarbonyl or hexyloxycarbonyl.

The term "an aminocarbonyl which may be substituted by a (lower) alkyl" includes aminocarbonyl which may be substituted by 1 or 2 of a straight chain or branched chain $C_1$–$C_6$ alkyl, such as carbamoyl, methylaminocarbonyl, ethylaminocarbonyl, propylaminocarbonyl, n-butylaminocarbonyl, pentylaminocarbonyl, hexylaminocarbonyl, dimethylaminocarbonyl, diethylaminocarbonyl, dipropylaminocarbonyl, dipentylaminocarbonyl, dihexylaminocarbonyl, N-methyl-N-propylaminocarbonyl, N-methyl-N-tert-butylaminocarbonyl or N-ethyl-N-pentylaminocarbonyl.

The term "a phenyl(lower)alkoxycarbonyl" includes phenylalkoxycarbonyl in which alkoxy moiety is a straight chain or branched chain $C_1$–$C_6$ alkoxy, such as benzyloxycarbonyl, 2-phenylethoxycarbonyl, 1-phenylethoxycarbonyl, 3-phenylpropoxycarbonyl, 4-phenylbutoxycarbonyl, 1,1-dimethyl-2-phenylethoxycarbonyl, 5-phenylpentyloxycarbonyl, 6-phenylhexyloxycarbonyl or 2-methyl-3-phenylpropoxycarbonyl.

The term "an amino(lower)alkanoyl which may be substituted by a phenyl(lower)alkoxycarbonyl" includes a straight chain or branched chain $C_2$–$C_6$ aminoalkanoyl which may be substituted by a phenylalkoxycarbonyl in which alkoxy moiety is a straight chain or branched chain $C_1$–$C_6$ alkoxy, such as 2-aminoacetyl, 3-aminopropionyl, 4-aminobutyryl, 5-aminopentanoyl, 6-aminohexanoyl, 2-benzyloxycarbonylaminoacetyl, 2-(2-phenylethoxycarbonylamino)acetyl, 2-(3-phenylpropoxycarbonylamino)acetyl, 3-(4-phenylbutoxycarbonylamino)propionyl, 4-(1,1-dimethyl-2-phenylethoxy-carbonylamino)butyryl, 5-(5-phenylpentyloxycarbonylamino)pentanoyl, 6-(6-phenylhexyloxycarbonylamino)hexanoyl or 2-(2-methyl-3-phenylpropoxycarbonylamino)acetyl.

The term "a (lower) alkoxycarbonyl(lower)alkyl" includes alkoxycarbonylalkyl in which alkoxy and alkyl moieties are a straight chain or branched chain $C_1$–$C_6$ alkoxy and alkyl, respectively, such as methoxycarbonylmethyl, ethoxycarbonylmethyl, 2-ethoxycarbonylethyl, 3-propoxycarbonylpropyl, 4-butoxycarbonylbutyl, 5-pentyloxycarbonylpentyl, 6-hexyloxycarbonylhexyl, 2-methoxycarbonylethyl, 3-methoxycarbonylpropyl, 3-ethoxycarbonylpropyl or 4-ethoxycarbonybutyl.

The term "a carboxy(lower)alkyl" includes carboxyalkyl in which alkyl moiety is a straight chain or branched chain $C_1$–$C_6$ alkyl, such as carboxymethyl, 2-carboxyethyl, 3-carboxypropyl, 4-carboxybutyl, 5-carboxypentyl, 6-carboxyhexyl, 1-carboxyethyl, 1,1-dimethyl-2-carboxyethyl or 2-methyl-3-carboxypropyl.

The term "an anilinocarbonyl(lower)alkyl" includes anilinocarbonylalkyl in which alkyl moiety is a straight chain or branched chain $C_1$–$C_6$ alkyl, such as anilinocarbonylmethyl, 2-anilinocaronylethyl, 1-anilinocarbonylethyl, 3-anilinocarbonylpropyl, 4-anilinocarbonylbutyl, 5-anilinocarbonylpentyl, 6-anilinocarbonylhexyl, 1,1-dimethyl- 2-anilinocarbonylethyl or 2-methyl-3-anilinocarbonylpropyl.

The term "an amino which may be substituted by a (lower) alkyl, a (lower) alkanoyl, a (lower) alkoxycarbonyl or a phenyl(lower)alkyl" includes amino which may be substituted by 1 or 2 of a straight chain or branched chain $C_1$–$C_6$ alkyl, a straight chain or branched chain $C_1$–$C_6$ alkanoyl, a straight chain or branched chain ($C_1$–$C_6$) alkoxycarbonyl or a phenylalkyl in which alkyl moiety is a straight chain or branched chain $C_1$–$C_6$ alkyl, such as amino, methylamino, ethylamino, propylamino, t-butylamino, pentylamino, hexylamino, dimethylamino, diethylamino, di-n-propylamino, di-n-butylamino, dipentylamino, dihexylamino, N-methyl-N-n-butylamino, N-methyl-N-pentylamino, N-ethyl-N-hexylamino, acetylamino, formylamino, propionylamino, butyrylamino, pentanoylamino, hexanoylamino, N-methyl-N-acetylamino, N-ethyl-N-propionylamino, N-methyl-N-butyryl-amino, N-n-propyl-N-pentanoylamino, N-ethyl-N-hexanoylamino, methoxycrbonylamino, ethoxycarbonylamino, propoxycarbonylamino, t-butoxycarbonylamino, pentyloxycarbonylamino, hexyloxycarbonylamino, butoxycarbonylamino, N-t-butoxycarbonyl-N-methylamino, N-t-butoxycarbonyl-N-ethylamino, N-t-butoxycarbonyl-N-benzylamino, benzylamino, (2-phenylethyl)amino, (1-phenylethyl)amino, (3-phenylpropyl)amino, (4-phenylbutyl)amino, (5-phenylpentyl)amino or (6-phenylhexyl)amino.

The term "a 2(5H)-furanone which may be substituted by 1 or 2 of halogen atoms" includes 2(5H)-furanone which may be substituted by 1 or 2 of halogen atoms, such as 2(5H)-furanon-5-yl, 3,4-dibromo-2(5H)-furanon-5-yl, 3,4-dichloro-2(5H)-furanon-5-yl, 3-chloro-2(5H)-furanon-5-yl, 4-fluoro-2(5H)-furanon-5-yl or 3-iodo-2(5H)-furanon-5-yl.

The term "a sulfo(lower)alkyl" includes sulfoalkyl in which alkyl moiety is a straight chain or branched chain $C_1$–$C_6$ alkyl, such as sulfomethyl, 2-sulfoethyl, 1-sulfoethyl, 3-sulfopropyl, 4-sulfobutyl, 5-sulfopentyl, 6-sulfohexyl, 1,1-dimethyl-2-sulfoethyl or 2-methyl-3-sulfopropyl.

The term "a (lower) alkylsulfonyl which may be substituted by 1 to 3 of halogen atoms" includes a straight chain or branched chain $C_1$–$C_6$ alkylsulfonyl which may be substituted by 1 to 3 of halogen atoms, such as methyl-sulfonyl, ethylsulfonyl, isopropylsulfonyl, n-butylsulfonyl, pentylsulfonyl, hexylsulfonyl, trifluoromethylsufonyl, 2-fluoroethylsulfonyl, 3-fluoropropylsulfonyl, 4,4,4-trifluorobutylsulfonyl, 5-chloropentylsulfonyl, 6-bromohexylsulfonyl, 6-iodohexylsulfonyl, 2,2-difluoroethylsulfonyl or 2,3-dibromopropylsulfonyl.

The term "a (lower) alkoxy" includes a straight chain or branched chain $C_1$–$C_6$ alkoxy, such as methoxy, ethoxy, propoxy, isopropoxy, butoxy, tert-butoxy, pentyloxy or hexyloxy.

The term "a (lower) alkanoyloxy" includes a straight chain or branched chain $C_2$–$C_6$ alkanoyloxy, such as acetyloxy, propionyloxy, butyryloxy, isobutyryloxy, pentanoyloxy or hexanoyloxy.

The term "a (lower) alkenyl" includes a straight chain or branched chain $C_2$–$C_6$ alkenyl, such as vinyl, allyl, 2-butenyl, 3-butenyl, 1-methylallyl, 2-pentenyl or 2-hexenyl.

The term "a (lower) alkynyl" includes a straight chain or branched chain $C_2$–$C_6$ alkynyl, such as ethynyl, 2-propynyl, 2-butynyl, 3-butynyl, 1-methyl-2-propynyl, 2-pentynyl or 2-hexynyl.

The term "a 2-oxo-1,3-dioxolenemethyl which may be substituted by phenyl or a (lower) alkyl" includes 2-oxo-1, 3-dioxolenemethyl which may be substituted by phenyl or a straight chain or branched chain $C_1$–$C_6$ alkyl, such as (5-methyl-2-oxo-1,3-dioxolen-4-yl)methyl, (5-tert-butyl-2-oxo-1,3-dioxolen-4-yl)methyl, (5-phenyl-2-oxo-1,3-dioxolen-4-yl)methyl, (2-oxo-1,3-dioxolen-4-yl)methyl, (5-pentyl-2-oxo-1,3-dioxolen-4-yl)methyl, (5-hexyl-2-oxo-1,3-dioxolen-4-yl)methyl, (5-ethyl-2-oxo-1,3-dioxolen-4-yl)methyl or (5-propyl-2-oxo-1,3-dioxolen-4-yl)methyl.

The term "a 2-oxo-1,3-dioxolenemethylamino which may be substituted by phenyl or a (lower) alkyl" includes 2-oxo-1,3-dioxolenemethylamino which may be substituted by phenyl or a straight chain or branched chain $C_1$–$C_6$ alkyl, such as (5-methyl-2-oxo-1,3-dioxolen-4-yl)methylamino, (5-tert-butyl-2-oxo-1,3-dioxolen-4-yl)methylamino, (5-phenyl-2-oxo-1,3-dioxolen-4-yl)methylamino, (2-oxo-1, 3-dioxolen-4-yl)methylamino, (5-pentyl-2-oxo-1,3-dioxolen-4-yl)methylamino, (5-hexyl-2-oxo-1,3-dioxolen-4-yl)methylamino, (5-ethyl-2-oxo-1,3-dioxolen-4-yl) methylamino, or (5-propyl-2-oxo-1,3-dioxolen-4-yl) methylamino.

The term "a cycloalkylamino" includes $C_3$–$C_8$ cycloalkylamino, such as cyclopropylamino, cyclobutylamino, cyclopentylamino, cyclohexylamino, cycloheptylamino or cyclooctylamino.

The term "a (lower) alkylthio" includes a straight chain or branched chain $C_1$–$C_6$ alkylthio, such as methylthio, ethylthio, propylthio, isopropylthio, butylthio, tert-butylthio, penthylthio or hexylthio.

The term "a phenyl which may be substituted by 1 to 3 of substituents selected from the group consisting of a (lower) alkoxy, a halogen atom and hydroxy on phenyl ring" includes phenyl which may be substituted by 1 to 3 of substituents selected from the group consisting of a straight chain or branched chain $C_1$–$C_6$ alkoxy, a halogen atom and hydroxy on phenyl ring, such as phenyl, 4-methoxyphenyl, 3-ethoxyphenyl, 2-propoxyphenyl, 4-n-butoxyphenyl, 3-pentyloxyphenyl, 2-hexyloxyphenyl, 3,4-dimethoxyphenyl, 2,4,6-trimethoxyphenyl, 2-fluorophenyl, 4-fluorophenyl, 3-chlorophenyl, 4-chlorophenyl, 4-bromophenyl, 2-iodophenyl, 2,4-difluorophenyl, 2,6-difluorophenyl, 3,4-difluorophenyl, 2,5-difluorophenyl, 2,4-dichlorophenyl, 2,6-dibromophenyl, 2,4,6-trifluorophenyl, 3,4,6-trichlorophenyl, 4-fluoro-2-methoxyphenyl, 2-fluoro-4-hydroxyphenyl, 2-hydroxyphenyl, 3-hydroxyphenyl, 4-hydroxyphenyl, 2,3-dihydroxyphenyl, 2,4-dihydroxyphenyl or 2,4,6-trihydroxyphenyl.

The term "a (lower) alkyl which may be substituted by a halogen atom, a (lower) alkanoyloxy or hydroxy" includes, in addition to the above-mentioned (lower) alkyl, a straight chain or branched chain $C_1$–$C_6$ alkyl which is substituted by 1 to 3 of substituents selected from the group consisting of a halogen atom, a straight chain or branched chain $C_2$–$C_6$ alkanoyloxy or hydroxy, such as hydroxymethyl, 2-hydroxyethyl, 1-hydroxyethyl, 3-hydroxypropyl, 4-hydroxybutyl, 5-hydroxypentyl, 6-hydroxyhexyl, 3-chloropropyl, bromomethyl, 2-fluoroethyl, 4-chlorobutyl, 3-fluoropentyl, difluoromethyl, 2,3-dichlorohexyl, 2,2,2-trifluoroethyl, trifluoromethyl, acetyloxymethyl, 2-propionyloxyethyl, 3-butyryloxypropyl, 4-pentanoyloxybutyl, 5-hexanoyloxypentyl, 6-acetyloxyhexyl, propanoyloxymethyl, 1-acetyloxyethyl, 2-acetyloxyethyl or 2-hexanoyloxyethyl.

The compounds of the present invention of the above general formula [1] can be prepared by various processes and preferably prepared, for example, by the processes as shown in the following reaction schemes.

[Reaction scheme-I]

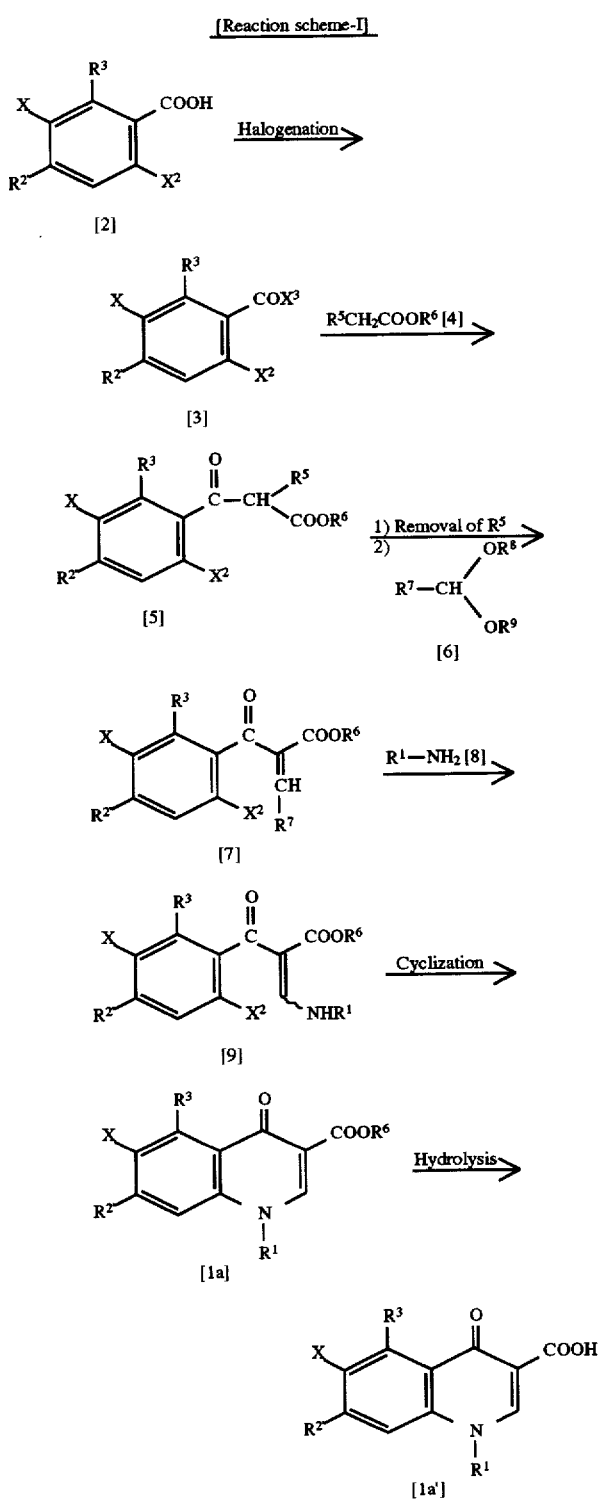

wherein $R^1$, $R^2$, $R^3$ and X are as defined above, $R^{2'}$ is a halogen atom or the $R^2$ group ($R^2$ is as defined above), $R^5$ is a group of the formula: —$COR^{10}$ (wherein $R^{10}$ is a (lower) alkyl) or a group of the formula: —$COOR^{11}$ (wherein $R^{11}$ is a (lower) alkyl), $R^6$ is a (lower) alkyl, $R^7$ is a group of the formula:

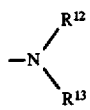

(wherein $R^{12}$ and $R^{13}$ are each a (lower) alkyl) or a (lower) alkoxy, $X^2$ and $X^3$ are each a halogen atom, $R^8$ and $R^9$ are each a (lower) alkyl.

The halogenation of the compound [2] is carried out by reacting with a halogenating agent in the presence or absence of a solvent. The solvent includes aromatic hydrocarbons such as benzene, toluene and xylene, halogenated hydrocarbons such as dichloromethane, chloroform and carbon tetrachloride, ethers such as dioxane, tetrahydrofuran and diethyl ether, dimethylformamide (DMF), dimethyl sulfoxide (DMSO), and the like. The halogenating agent may be any conventional halogenating agents which can convert hydroxy in carboxy group into a halogen atom, and includes, for example, thionyl chloride, phosphorus oxychloride, phosphorus oxybromide, phosphorus pentachloride, phosphorus pentabromide, and the like. The amounts of the compound [2] and the halogenating agent are not particularly limited, but, in case of using no solvent, the halogenating agent is usually used in a large excess amount, and in case of using a solvent, the halogenating agent is usually used in an amount of at least 1 mole, preferably 2 to 4 moles, per 1 mole of the compound [2]. The reaction temperature and the reaction period of time are not particularly limited either, but the reaction is usually carried out at a temperature of from room temperature to around 100° C. for about 30 minutes to about 6 hours.

The reaction between the compound [3] and the compound [4] is carried out in a suitable solvent in the presence of a basic compound. The solvent used in the reaction may be any conventional solvents unless they give any undesirable effect on the reaction, and includes, for example, water, ethers such as diethyl ether, dioxane, tetrahydrofuran, monoglyme and diglyme, alcohols such as methanol, ethanol and isopropanol, aromatic hydrocarbons such as benzene, toluene and xylene, aliphatic hydrocarbons such as n-hexane, heptane, cyclohexane and ligroin, amines such as pyridine and N,N-dimethylaniline, halogenated hydrocarbons such as chloroform, dichloromethane and carbon tetrachloride, aprotic polar solvents such as DMF, DMSO and hexamethylphosphoramide (HMPA), and a mixture of these solvents. The basic compound employed in the reacion includes inorganic bases such as metallic sodium, metallic potassium, metallic magnesium, sodium hydride, sodium amide, sodium hydroxide, potassium hydroxide, sodium carbonate, potassium carbonate and sodium hydrogen carbonate, metal alcoholates such as sodium methylate and sodium ethylate, and organic bases such as pyridine, piperidine, quinoline, triethylamine and N,N-dimethylaniline. The reaction is usually carried out at a temperature of from around 0° C. to around 150° C., preferably from around 0° C. to around 120° C. for about 0.5 to about 20 hours. The compound [4] is usually used in an amount of at least 1 mole, preferably 1 to 2 moles, per 1 mole of the compound [3]. The basic compound is usually used in an amount of at least 1 mole, preferably 1 to 2 moles, per 1 mole of the compound [3].

The compound [5] wherein $R^5$ is the group of the formula: —$COR^{10}$ is subjected to the reaction for removal of the group: —$COR^{10}$ in a Suitable solvent in the presence of a basic compound. The solvent used in the reaction includes, for example, ethers such as diethyl ether, dioxane, tetrahydrofuran, monoglyme and diglyme, aromatic hydrocarbons such as benzene, toluene and xylene, aliphatic hydrocarbons such as n-hexane, heptane and cyclohexane, aprotic polar solvents such as DMF, DMSO and HMPA, and the like. The basic compound includes ammonia gas, aqueous ammonia, ammonium salts such as ammonium chloride, primary or secondary amines such as ethylamine, diethylamine and piperidine, and the like. The reaction is usually carried out at a temperature of from around 0° C. to around 150° C., preferably from room temperature to around 100° C., for about 1 to about 20 hours.

The compound [5] wherein $R^5$ is a group of the formula: —$COOR^{11}$ is subjected to the reaction for removal of the group: —$COOR^{11}$ in an aqueous solution in the presence of an acid catalyst. The acid catalyst used in the reaction includes mineral acids such as hydrochloric acid and sulfuric acid, and organic acids such as p-toluenesulfonic acid. The reaction is usually carried out at a temperature of from around 0° C. to around 150° C., preferably from room temperature to around 100° C., for about 1 to about 20 hours.

The reaction between the obtained $R^5$ group-removed compound and the compound [6] is carried out in a suitable solvent. The solvent employed in the reaction may be any solvents which are used in the above reaction for the removal of the $R^4$ group in addition to anhydrous (lower) alkanoic acid such as acetic anhydride. The reaction is usually carried out at a temperature of from around 0° C. to around 200° C., preferably from around 0° C. to around 150° C., for about 0.5 to about 10 hours. The comound [6] is usually used in an equimolar to large excess amount, preferably in an equimolar to 2 times molar amount based on the compound [5]. In case of using a compound [6] wherein $R^7$ is a (lower) alkoxy group, the reaction may also be carried out by using acid anhydrides such as acetic anhydride as a solvent as well as the above-mentioned solvents at a temperature of from around 0° C. to around 200° C., preferably from around 0° C. to around 170° C.

The reaction be6ween the compound [7] and the compound [8] is carried out in a suitable solvent. The solvent employed in the reaction may be any conventional solvents unless they give any undesirable effect on the reaction, and includes, for example, alcohols such as methanol, ethanol and propanol, ethers such as diethyl ether, dioxane, tetrahydrofuran, monoglyme and diglyme, aromatic hydrocarbons such as benzene, toluene and xylene, aliphatic hydrocarbons such as n-hexane, heptane, cyclohexane and ligroin, halogenated hydrocarbons such as chloroform, methylene chloride and carbon tetrachloride, aprotic polar solvents such as DMF, DMSO and HMPA, and the like. The reaction is usually carried out at a temperature of from around 0° C. to around 150° C., preferably from room temperature to around 100° C., for about 0.1 to about 15 hours. The compound [8] is usually used in an amount of at least 1 mole, preferably 1 to 2 moles, per 1 mole of the compound [7]. In the reaction, a basic compound may optionally be added. Such basic compound may be any basic compounds which are used in the above reaction between the compound [3] and the compound [4].

The cyclization of the compound [9] is carried out in a suitable solvent in the presence of a basic compound. The solvent employed in the reaction may be any conventional solvents unless they give any undesirable effect on the reaction, and includes, for example, ethers such as diethyl ether, dioxane, tetrahydrofuran, monoglyme and diglyme, aliphatic hydrocarbons such as n-hexane, heptane and ligroin, halogenated hydrocarbons such as chloroform, methylene chloride and carbon tetrachloride, aprotic polar solvents such as DMF, DMSO and HMPA, and the like. The basic compound employed in the reaction includes inorganic bases such as metallic sodium, metallic potassium, sodium hydride, sodium amide, sodium hydroxide, potassium hydroxide, sodium carbonate and potassium carbonate, metal alcoholates such as sodium methylate and sodium ethylate, organic bases such as 1,8-diazabicyclo[5.4.0]undecene-7 (DBU), N-benzyltrimethylammonium hydroxide and tetrabutylammonium hydroxide, and the like. The reaction is usually carried out at a temperature of from around 0° C. to around 200° C., preferably from room temperature to around 150° C., for about 0.5 to about 15 hours. The basic compound is usually used in an amount of at least 1 mole, preferably 1 to 2 moles, per 1 mole of the compound [9].

The hydrolysis of the compound [1a] can be carried out under the conditions of conventional hydrolysis, for instance, in the presence of a basic compound such as sodium hydroxide, potassium hydroxide, barium hydroxide or potassium carbonate, a mineral acid such as sulfuric acid, hydrochloric acid or nitric acid, or an organic acid such as acetic acid or aromatic sulfonic acids, in a solvent including water, alcohols such as methanol, ethanol and isopropanol, ketones such as acetone and methyl ethyl ketone, ethers such as dioxane and ethylene glycol diethyl ether, acetic acid, or a mixture thereof. The reaction is usually carried out at a temperature of from room temperature to around 200° C., preferably from room temperature to around 150° C., for about 0.1 to about 30 hours. By the reaction, there is produced the compound [1a'].

[Reaction Scheme-II]

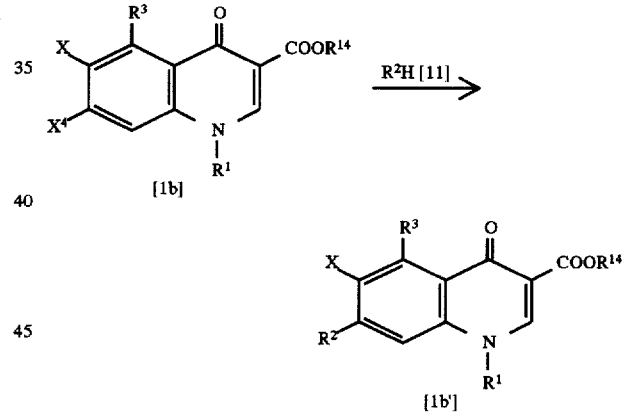

wherein $R^1$, $R^2$, $R^3$ and X are as defined above, $X^4$ is a halogen atom, and $R^{14}$ is hydrogen atom or a group of the formula:

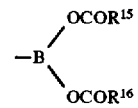

(wherein $R^{15}$ and $R^{16}$ are each an alkyl).

For conducting the reaction between the compound [1b] and the comound [11], both compounds are used in a wide range of ratio, and the compound [11] is usually used in an amount of at least 1 mole, preferably about 1 to about 5 moles, per 1 mole of the compound [1b]. The reaction is carried out in an innert solvent, which includes, for example, water, alcohols such as methanol, ethanol, isopropanol, butanol, amyl alcohol and isoamyl alcohol, aromatic hydrocarbons such as benzene, toluene and xylene, ethers such as tetrahydrofuran, dioxane and diglyme, dimethylacetamide, DMF, DMSO, HMPA, N-methylpyrrolidone, and the like and a mixture thereof. Among these solvents, the preferred one is DMF, DMSO, HMPA, and N-methylpyrrolidone. The reaction may also be carried out in the presence of an acid-removing agent, including inorganic carbonates such as sodium carbonate, potassium carbonate, sodium hydrogen carbonate and potassium hydrogen carbonate and organic bases such as pyridine, quinoline and triethylamine. An alkaline methal halide such as potassium fluoride may also be added to the reaction mixture. The reaction is usually carried out under a pressure of from 1 to 20 atm., preferably from 1 to 10 atm., at a temperature of from room temperature to around 250° C., preferably from room temperature to around 200° C., for about 10 minutes to about 30 hours.

The compound [1b'] wherein $R^{14}$ is a group of the formula:

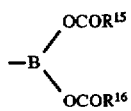

can be converted into the corresponding compound [1b'] wherein $R^{14}$ is hydrogen atom by treating the former compound with an acid or a base to decompose the chelate compound. The acid employed in the reaction includes mineral acids such as hydrochloric acid and sulfuric acid, and organic acids such as acetic acid and p-toluenesulfonic acid. The base employed in the reaction includes mineral bases such as sodium hydroxide, potassium hydroxide, sodium hydrogen carbonate, potassium hydrogen carbonate and potassium carbonate, and organic bases such as triethylamine. The reaction favorably proceeds at a temperature of from around 0° C. to around 150° C., preferably from around 0° C. to around 100° C. The acid or the base may be used in an amount of at least 1 mole, preferably 1 to 10 moles, per 1 mole of the starting compound.

[Reaction scheme-III]

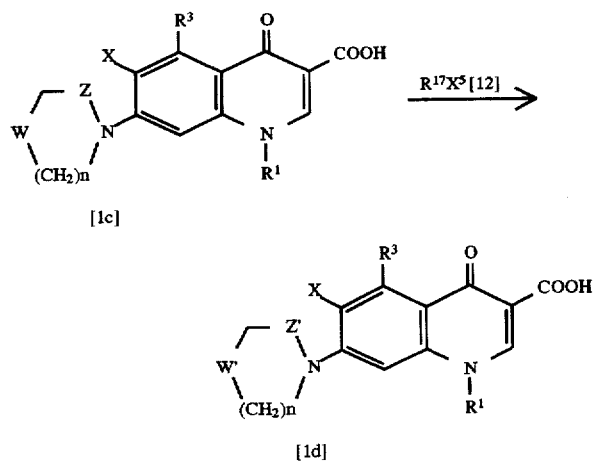

wherein X, $R^1$ and $R^3$ are as defined above, either Z or W is —$CH_2$— and the other is —NH, n is an integer of 1 to 3, $R^{17}$ is a (lower) alkyl; a cycloalkyl; a phenyl(lower)alkyl in which phenyl ring may be substituted by a (lower) alkoxy, nitro or amino; a phenyl which may be substituted by a halogen atom or a (lower) alkyl which may be substituted by 1 to 3 of halogen atoms; a pyridyl; a (lower) alkyl having 1 to 3 of substituents selected from the group consisting of hydroxy, an amino which may be substituted by 1 or 2 substituents of a (lower) alkyl, a (lower) alkanoyl, a cycloalkyl or a (lower) alkoxycarbonyl, a (lower) alkoxy and a halogen atom; a (lower) alkanoyl which may be substituted by 1 to 7 of halogen atoms; a (lower) alkenylcarbonyl having 1 to 3 of substituents selected from the group consisting of a halogen atom and a carboxy; a (lower) alkoxycarbonyl; an aminocarbonyl which may be substituted by a (lower) alkyl; a phenyl(lower)alkoxycarbonyl; an amino(lower)alkanoyl which may be substituted by a phenyl(lower) alkoxycarbonyl; a (lower) alkoxycarbonyl(lower)alkyl; a carboxy(lower)alkyl; an anilinocarbonyl(lower)alkyl; a (lower) alkylsulfonyl which may be substituted by 1 to 3 of halogen atoms; a sulfo(lower)alkyl; a (lower) alkenyl or a (lower) alkynyl, $X^5$ is a halogen atom, and either Z' or W' is —$CH_2$— and the other is —$NR^{17}$.

The reaction between the compound [1c] and the compound [12] is carried out in a suitable solvent in the presence of a hydrogen halide-removing agent. The solvent includes water, alcohols such as methanol, ethanol and isopropanol, ketones such as acetone and methyl ethyl ketone, ethers such as diethyl ether and dioxane, aromatic hydrocarbons such as benzene, toluene and xylene, and the like. The hydrogen halide-removing agent includes inorganic bases such as sodium hydroxide, potassium hydroxide, sodium carbonate and potassium carbonate, alkaline metals such as sodium and potassium, and organic bases such as pyridine and piperidine. If necessary, copper powders, copper halides such as copper iodide or alkaline metal halides such as sodium iodide and potassium iodide may also be employed. The compound [12] is usually used in an equimolar to large excess amount, preferably 1 to 3 moles, per 1 mole of the compound [1c]. The reaction is usually carried out at a temperature of from room temperature to around 150° C., preferably from around 50° C. to around 120° C., for about 1 to about 12 hours.

[Reaction scheme - IV]

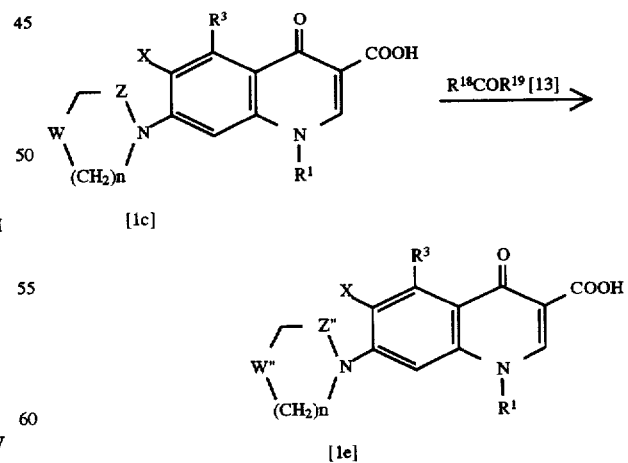

wherein $R^1$, $R^3$, Z, W, n and X are as defined above, $R^{18}$ and $R^{19}$ are each hydrogen atom or a lower alkyl, and either Z" or W" is —$CH_2$— and the other is

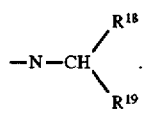

The reaction between the compound [1c] and the compound [13] is carried out in the presence or absence of a solvent in the presence of a reducing agent. The solvent employed in the reaction includes, for example, water, alcohols such as methanol, ethanol and isopropanol, lower alkanoic acids such as formic acid and acetic acid, ethers such as dioxane, diethyl ether, diglyme and tetrahydrofuran, aromatic hydrocarbons such as benzen, xylene and toluene, and the like. The reducing agent includes formic acid, alkaline metal or alkaline earth metal salts of formic acid such as sodium formate, reducing agents for hydrogenation such as sodium borohydride, sodium cyanoborohydride and lithium aluminum hydride, catalysts for catalytic reduction such as palladium black, palladium carbon, platinum oxide, platinum black and Raney nickel, and the like. In case of using formic acid as the reducing agent, the reaction is usually carried out at a temperature of from room temperature to around 200° C., preferably from around 50° C. to around 150° C., for about 1 to about 10 hours. Formic acid is preferably used in a large excess amount to the compound [1c]. Besides, in case of using a reducing agent for hydrogenation, the reaction is usually carried out at a temperature of from around −30° C. to around 100° C., preferably from around 0° C. to around 70° C., for about 30 minutes to about 12 hours. The reducing agent is usually used in an amount of from 1 to 20 moles, preferably from 1 to 6 moles, per 1 mole of the compound [1c]. In case of using lithium aluminum hydride as the reducing agent, a preferable solvent includes ethers such as diethyl ether, dioxane, tetrahydrofuran and diglyme, aromatic hydrocarbons such as benzene, toluene and xylene, and the like. In case of using a catalyst for catalytic reduction, the reaction is usually carried out under a hydrogen pressure of from ordinary pressure to 20 atm., preferably from ordinary pressure to 10 atm., at a temperature of from −30° C. to 100° C., preferably from 0° C. to 60° C., for 1 to 12 hours. The catalyst is usually used in an amount of from 0.1 to 40% by weight, preferably from 0.1 to 20% by weight, of the compound [1c]. The compound [13] is usually used in an amount of at least 1 mole, preferably 1 mole to a large excess amount, per 1 mole of the compound [1c].

In the reaction scheme-II, the compounds of the formula [1b] wherein $R^{14}$ is a group:

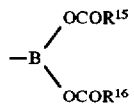

can be prepared, for example, by the process as shown in the following reaction scheme-V.

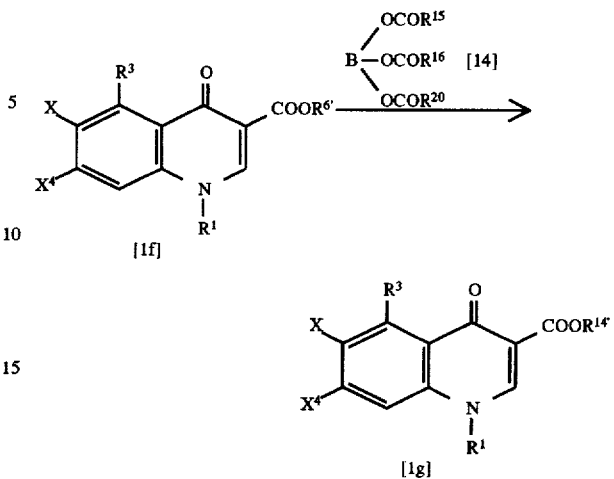

wherein $R^1$, $R^3$, X, $X^4$, $R^{15}$ and $R^{16}$ are as defined above, $R^{6'}$ is a (lower) alkyl or hydrogen atom, $R^{14'}$ is a group:

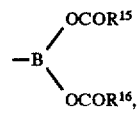

and $R^{20}$ is a (lower) alkyl.

The reaction between the compound [1f] and the compound [14] is carried out in a suitable solvent. The solvent employed in the reaction includes, for example, the solvents employed in the reaction between the $R^5$ group-removed compound and the compound [6] in the above reaction scheme-I. The reaction is usually carried out at a temperature of from room temperature to around 200° C., preferably from room temperature to around 150° C., for about 10 minutes to about 5 hours. The compound [14] is usually used in an amount of at least 1 mole, preferably 1 to 10 moles, per 1 mole of the compound [1f].

The compounds [8] employed in the reaction scheme-I are novel or known compounds, which can be prepared, for example, by the process as shown in the following reaction scheme-VI.

[Reaction scheme-VI]

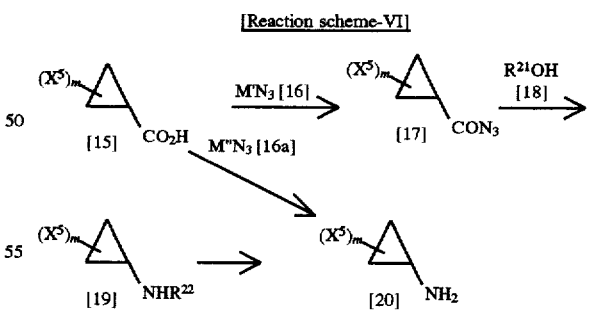

wherein $X^5$ is a halogen atom, $R^{21}$ is a phenyl(lower)alkyl, $R^{22}$ is a phenyl(lower)alkoxycarbonyl, m is an integer of 1 to 3, M' is an alkaline metal such as sodium or potassium, and M" is hydrogen atom or M'.

The reaction between the compound [15] and the compound [16] can be carried out under reaction conditions usually employed in a reaction for forming an amide bond. For forming an amide bond, known reaction conditions for the amide bond formation can be employed, for example, (a)

a mixed acid anhydride process: a process which comprises reacting the carboxylic acid [15] with an alkyl halocarboxylate to give a mixed acid anhydride, which is then reacted with the azide [16]; (b) an active ester process: a process which comprises converting the carboxylic acid [15] into an active ester such as p-nitrophenyl ester, N-hydroxysuccinimide ester or 1-hydroxybenzotriazole ester, and then reacting the resultant ester with the azide [16]; (c) a carbodiimide process: a process which comprises condensing the carboxylic acid [15] with the azide [16] in the presence of an activating agent such as dicyclohexylcarbodiimide or carbonyldiimidazole; and (d) other processes: a process which comprises converting the carboxylic acid [15] into the carboxylic anhydride using a dehydration agent such as acetic anhydride, and then reacting the resultant anhydride with the azide [16], a process which comprises reacting an ester from the carboxylic acid [15] and a lower alcohol with the azide [16] under a high pressure at a high temperature, or a process which comprises reacting an acid halide of the carboxylic acid [15], i.e. acyl halide with the azide [16].

The mixed acid anhydride used in the above mixed acid anhydride process can be obtained by a conventional Schotten-Baumann reaction, and the resultant anhydride is reacted with the azide [16], usually without separating it from the reaction mixture, to prepare the compound [17]. The Schotten-Baumann reaction is carried out in the presence of a basic compound. The basic compound which can be employed in the reaction includes those usually employed in the Schotten-Baumann reaction, for example, organic bases such as triethylamine, trimethylamine, pyridine, dimethylaniline, N-methylmorpholine, 1,5-diazabicyclo [4.3.0] nonene-5 (DBN), 1,8-diazabicyclo [5,4,0] undecene-7 (DBU) and 1,4-diazabicyclo [2,2,2] octane (DABCO), and inorganic bases such as potassium carbonate, sodium carbonate, potassium hydrogen carbonate and sodium hydrogen carbonate.- The reaction is usually carried out at a temperature of from around −20° C. to around 100° C., preferably from around 0° C. to around 50° C., for 5 minutes to 10 hours, preferably 5 minutes to 2 hours. The reaction between the obtained mixed acid anhydride and the azide [16] is usually carried out at a temperature of from around −20° C. to around 150° C., preferably from around 0° C. to around 50° C., for 5 minutes to 10 hours, preferably for 5 minutes to 5 hours. The mixed acid anhydride process is usually carried out in a solvent. The solvent may be any which is usually employed in the mixed acid anhydride process, including water, halogenated hydrocarbons such as methylene chloride, chloroform and dichloroethane, aromatic-hydrocarbons such as benzene, toluene and xylene, ethers such as diethyl ether, tetrahydrofuran and dimethoxyethane, esters such as methyl acetate and ethyl acetate, ketones such as acetone, aprotic polar solvents such as DMF, DMSO and HMPA, and a mixture thereof. The alkyl halocarboxylate used in the mixed acid anhydride process includes, for example, methyl chloroformate, methyl bromoformate, ethyl chloroformate, ethyl bromoformate, isobutyl chloroformate, and the like.

The azide [16] is usually used in an amount of at least 1 mole, preferably 1 to 1.5 moles, per 1 mole of the carboxylic acid [15].

In case of using the process of reacting an acyl halide with the azide [16], the reaction is carried out in a suitable solvent in the presence of a basic compound. The basic compound used in the reaction may be any known basic compounds, including, for example, sodium hydroxide, potassium hydroxide, sodium hydride, potassium hydride, silver carbonate, and metal alcoholates such as sodium methylate and sodium ethylate, in addition to the basic compound employed in the above Schotten-Baumann reaction. The solvent used in the reaction includes, for example, alcohols such as methanol, ethanol, propanol, butanol, 3-methoxy-1-butanol, ethyl cellosolve and methyl cellosolve, pyridine, acetone, acetonitrile, the solvents employed in the above mixed acid anhydride process, and a mixture thereof. Although the ratio of the azide [16] and an acyl halide employed is not particularly limited, the acyl halide is usually used in an amount of at least 1 mole, preferably 1 to 5 moles, per 1 mole of the azide [16]. The reaction is usually carried out at a temperature of from around −30° to around 180° C., preferably from around 0° C. to around 150° C., for about 5 minutes to about 30 hours. The compound [17] thus prepared may be used in a subsequent reaction without separating it from the reaction mixture.

The reaction between the compound [17] and the compound [18] is usually carried out at a temperature of from around 0° C. to around 150° C., preferably from room temperature to around 100° C., for 1 to 15 hours, in a suitable solvent or in the absence a solvent. The compound [18] is usually used in an amount of at least 1 mole, preferably 1 to 2 moles, per 1 mole of the compound [17].

The reaction of converting the compound [19] into the compound [20] can be carried out under the same reaction conditions as used in the reaction for removing a phenyl (lower) alkyl or a phenyl (lower) alkoxycarbonyl on the heterocyclic ring attached to the above compound [1].

The reaction of directly converting the compound [15] into the compound [20] is generally referred to as Schmidt reaction, and carried out in a suitable solvent in the presence of an acid. The acid employed in the reaction includes mineral acids such as sulfuric acid and hydrochloric acid, phosphorus compounds such as phosphorus oxychloride, phosphorus pentachloride, phosphorus trichloride and phosphorus pentoxide, thionyl chloride, iron [III] chloride, aluminum chloride, stannic chloride, sulfoacetic acid, phosphoric acid, and the like. The solvent includes aromatic hydrocarbons such as benzene, toluene and xylene, halogenated hydrocarbons such as chloroform, dichloromethane and carbon tetrachloride, and the like. The reaction is usually carried out at a temperature of from around 0° C. to around 150° C., preferably from around 0° C. to around 100° C., for about 0.5 to about 10 hours. The compound [16a] is usually used in an amount of at least 1 mole, preferably 1 to 2 moles, per 1 mole of the compound [15].

[Reaction scheme-VII]

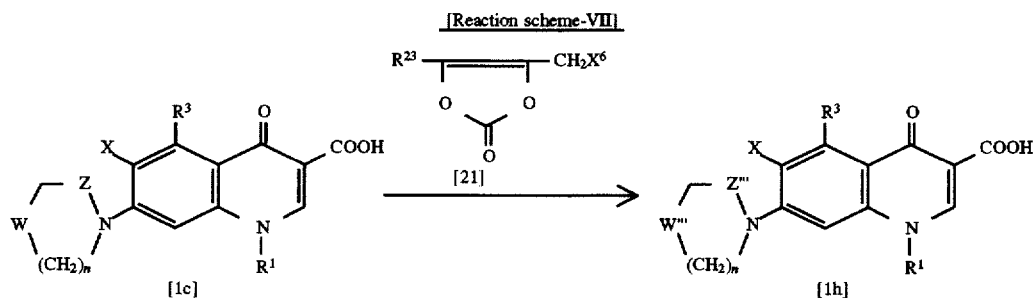

wherein $R^{23}$ is phenyl, a lower alkyl or hydrogen atom, $X^6$ is a halogen atom, either $Z'''$ or $W'''$ is —$CH_2$— and the other is a group:

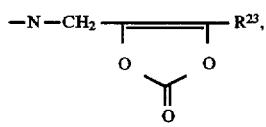

and $R^1$, $R^3$, Z, W, X and n are as defined above.

The reaction between the compound [1c] and the compound [21] can be carried out under the same reaction conditions as employed in the reaction between the compound [1b] and the compound [11] in the above reaction scheme-II.

Among the compounds [1], the compound in which the heterocyclic ring is substituted by (a) a phenyl(lower)alkyl in which phenyl ring may be substituted by a (lower) alkoxy, nitro or amino; (b) a (lower) alkanoyl which may be substituted by 1 to 7 of halogen atoms, a (lower) alkenylcarbonyl having 1 to 3 of substituents selected from the group consisting of a halogen atom and a carboxy; (c) a (lower) alkoxycarbonyl; (d) an aminocarbonyl which may be substituted by a (lower) alkyl; (e) a phenyl(lower) alkoxycarbonyl; (f) an amino(lower)alkanoyl which may be substituted by a phenyl(lower)alkoxycarbonyl; (g) phthalide; (h) a 2(5H)-furanone which may be substituted by 1 or 2 of halogen atoms; or (i) a 2-oxo-1,3-dioxolenemethyl which may be substituted by phenyl or a (lower) alkyl can be converted into the compound [1] in which the heterocyclic ring is not substituted, for example, using the following methods.

The compound [1] in which the heterocyclic ring is substituted by (a) or (e) can be converted into the compound [1] in which the heterocyclic ring is not substituted, by treating the former compound in a suitable solvent such as, for example, water, a (lower) alcohol such as methanol, ethanol or isopropanol, an ether such as dioxane or tetrahydrofuran, acetic acid, or a mixture thereof, in the presence of a catalyst for catalytic reduction such as palladium carbon or palladium black, under a hydrogen pressure of from 1 to 10 atom., at a temperature of from around 0° C. to around 100° C., for about 0.5 to about 10 hours, wherein a mineral acid such as hydrochloric acid may be added to the reaction mixture, or by heating the former compound in an aqueous hydrobromic acid solution, to remove the phenyl (lower)alkyl such as benzyl or the phenyl(lower) alkoxycarbonyl.

The compound [1] in which the heterocyclic ring is substituted by any of the substituents (b) to (i) can be converted into the compound [1] in which the heterocyclic ring is not substituted, by hydrolyzing the former compound under the same reaction conditions as employed in the hydrolysis of the above compound [1a].

The compound [1] in which the heterocyclic ring is substituted by amino can be converted into the compound [1]in which the heterocyclic ring is substituted by a group:

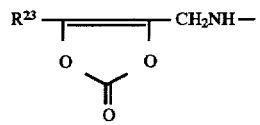

by using the same reaction conditions as employed in the reaction between the compound [1c] and the compound [21] in the above reaction scheme-VII. The compound [1] in which the heterocyclic ring is substituted by a group:

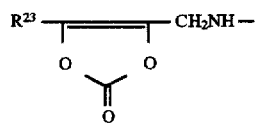

can also be converted into the compound [1] in which the heterocyclic ring is substituted by amino, by hydrolyzing the former compound under the same reaction conditions as employed in the hydrolysis of the above compound [1a].

[Reaction scheme-VIII]

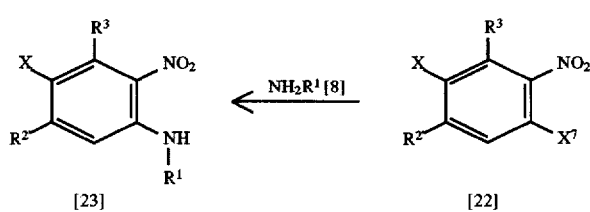

-continued
[Reaction scheme-VIII]

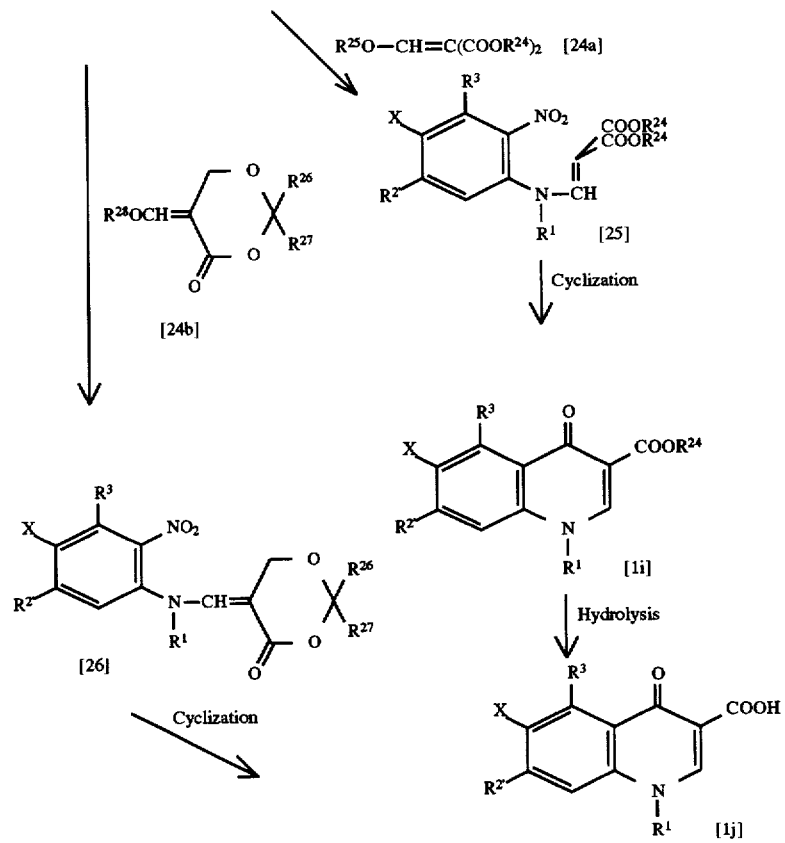

wherein $R^1$, $R^2$, $R^3$ and X are as defined above, $R^{24}$, $R^{25}$, $R^{26}$, $R^{27}$ and $R^{28}$ are each a (lower) alkyl, and $X^7$ is a halogen atom.

The reaction between the compound [22] and the compound [8] can be carried out under the same reaction conditions as employed in the reaction between the compound [1b] and the compound [11] in the above reaction scheme-II.

The reaction between the compound [23] and the compound [24a] or [24b] is carried out in the presence or absence of a solvent, preferably in the absence of a solvent. The solvent used in the reaction includes, for example, alcohols such as methanol, ethanol and isopropanol, aromatic hydrocarbons such as benzene and toluene, polar solvents such as acetonitrile, DMF, DMSO and HMPA, and the like. The compound [24a] or [24b] is usually used in an amount of at least 1 mole, preferably 1 to 1.5 moles, per 1 mole of the compound [23]. The reaction is usually carried out at a temperature of from room temperature to around 200° C., preferably from around 60° C. to around 200° C., for about 0.5 to about 25 hours.

The cyclization of the compound [25] or [26] can be carried out according to various known methods for the cyclization, including a heating method, a method using an acidic compound such as phosphorus oxychloride, phosphorus pentachloride, phosphorus trichloride, thionyl chloride, conc. sulfuric acid or polyphosphoric acid, and the like. In case of using the heating method, the reaction is usually carried out in a high b.p. solvent such as a high b.p. hydrocarbon or a high b.p. ether such as tetralin, diphenyl ether or diethylene glycol dimethyl ether at a temperature of from 100° C. to 250° C., preferably from 150° C. to 200° C. In case of using the method with an acidic compound, the acidic compound is usually used in an equimolar to a large excess amount, preferably 10 to 20 moles, per 1 mole of the compound [25] or [26]. The reaction is usually carried out in the presence or absence of a suitable solvent at a temperature of from room temperature to 150° C. for about 0.1 to about 6 hours. The solvent includes acid anhydrides such as acetic anhydride in addition to the solvents employed in the cyclization of the above compound [9].

The hydrolysis of the compound [1i] can be carried out under the same reaction conditions as employed in the hydrolysis of the compound [1a] in the above reaction scheme-I.

The compound [1j] in which $R^{2'}$ is a 5- to 9-membered saturated or unsaturated heterocyclic ring having a (lower) alkoxycarbonyl on the secondary nitrogen atom can be converted into the corresponding compound in which $R^{2'}$ is a 5- to 9-membered saturated or unsaturated heterocyclic ring having no substituent on the secondary nitrogen atom by treating the former compound under the same reaction conditions as employed in the hydrolysis of the compound [1a] in the above reaction scheme-I.

The compound [22] employed as the starting material in the above reaction scheme-VIII can be prepared, for example, by the processes as shown in the following reaction schemes-IX to XI.

[Reaction scheme-IX]

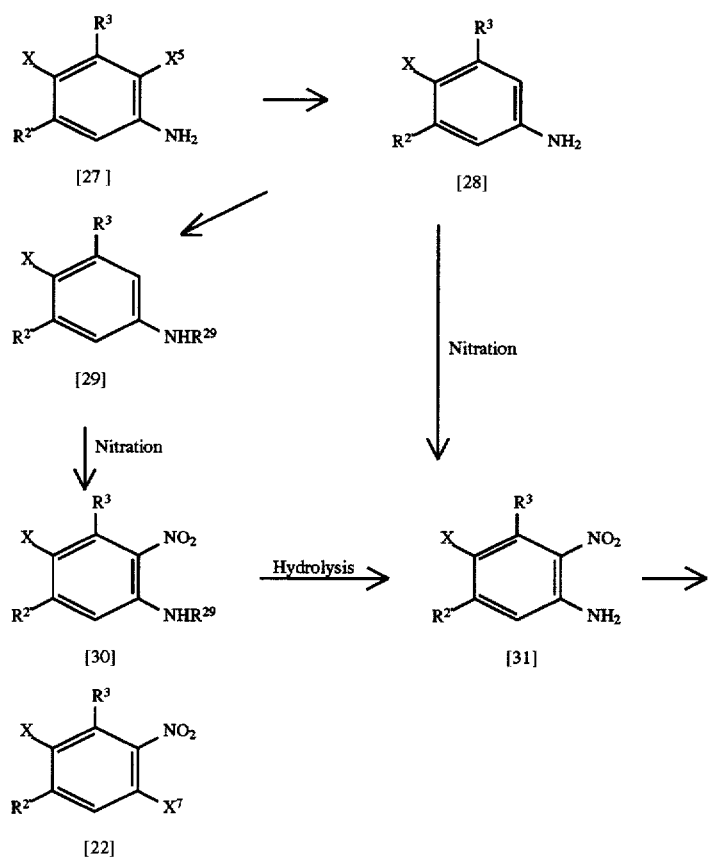

wherein $R^1$, $R^2$, $R^3$, X, $X^5$ and $X^7$ are as defined above and $R^{29}$ is a (lower) alkanoyl.

The reaction or converting the compound [27] to the compound [28] can be carried out under the same reaciton conditions as employed in the desulfurization of the compound [41] or [45] in reaction scheme-X as disclosed hereinafter.

The reaction of converting the compound [28] into the compound [29] is carried out in the presence of a (lower) alkanoylating agent, which includes a (lower) alkanoic acid such as formic acid, acetic acid or propionic acid, a (lower) alkanoic acid anhydride such as acetic anhydride, a (lower) alkanoic acid halide such as acetyl chloride or propionyl bromide, or the like. In case of using an acid anhydride or an acid halide as the (lower) alkanoylating agent, a basic compound may also be employed. The basic compound includes, for example, alkali metals such as metallic sodium and metallic potassium; hydroxides, carbonates or hydrogen carbonates of these alkali metals; organic bases such as pyridine and piperidine, and the like. The reaction can be carried out in either the presence or the absence of a solvent, usually in the presence of a suitable solvent. The solvent includes, for example, ketones such as acetone and methyl ethyl ketone, ethers such as diethyl ether and dioxane, aromatic hydrocarbons such as benzene, toluene and xylene, acetic acid, acetic anhydride, water, pyridine, and the like. The (lower) alkanoylating agent is used in an amount of at least 1 mole per 1 mole of the compound [28], usually in an equimolar to a large excess amount. The reaction is usually carried out at a temperature of from around 0° C. to around 150° C., preferably from around 0° C. to around 100° C., for about 5 minutes to about 15 hours. In case of using a (lower) alkanoic acid as the (lower) alkanoylating agent, a dehydrating agent is preferably employed, which includes mineral acids such as sulfuric acid and hydrochloric acid, sulfonic acids such as p-toluenesulfonic acid, benzenesulfonic acid and ethanesulfonic acid and the like, and the reaction is preferably carried out at a temperature of from around 50° C. to around 120° C.

The nitration of the compound [28] or [29] is carried out by treating the said compound with a nitrating agent such as fuming nitric acid, concd. nitric acid, a mixed acid (e.g. nitric acid plus sulfuric acid, fuming sulfuric acid, phosphoric acid or acetic anhydride, etc.), an alkali metal nitrate plus sulfuric acid, an anhydride of nitric acid and an organic acid such as acetyl nitrate or benzoyl nitrate, nitrogen tetraoxide, nitric acid plus mercury nitrate, nitrate of acetone cyanohydrin, an alkyl nitrate plus sulfuric acid or a polyphosphoric acid, without a solvent or in the presence of a solvent such as acetic acid, acetic anhydride or sulfuric acid. The nitrating agent is preferably used in an amount of 1 to 5 moles per 1 mole of the compound [28] or [29]. The reaction is usually carried out at a temperature of from around −10° C. to around 70° C. for about 10 minutes to about 24 hours.

The hydrolysis of the compound [30] is carried out under the same reaction conditions as employed in the hydrolysis of the above compound [1a].

The reaction of converting the compound [31] into the compound [22] can be carried out by converting the former compound into a diazonium salt thereof using sodium nitrite and an acid such as sulfuric acid, hydrochloric acid hydrobromic acid or boron fluoride in a solvent such as a (lower) alkanoic acid such as acetic acid or water, and then reacting the diazonium salt with a copper powder or a copper halide such as, for example, cuprous bromide, cuprous chloride or cupric chloride in the presence of a hydrohalogenic acid such as, for example, hydrobromic acid or hydrochloric acid, or reacting with potassium iodide in the presence or absence of a copper powder, preferably with a copper halide in the presence of a hydrohalogenic acid. The sodium nitrite is usually used in an amount of 1 to 2 moles, preferably 1 to 1.5 moles, per 1 mole of the compound [31], and the copper halide is usually used in an amount of 1 to 5 moles, preferably 1 to 4 moles, per 1 mole of the compound [22]. The reaction is usually carried out at a temperature of from around −20° C. to around 100° C., preferably from around −5° C. to around 100° C., for about 10 minutes to about 5 hours.

The halogen atoms of $R^{2'}$ and $X^9$ in the compound [22], the compound [1a], the compound [1a'] and the compound [33] described below can be converted into each other.

[Reaction scheme-X]

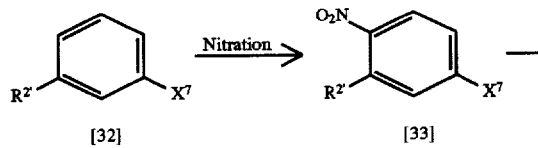

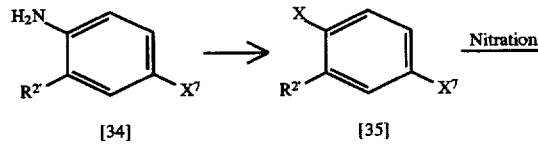

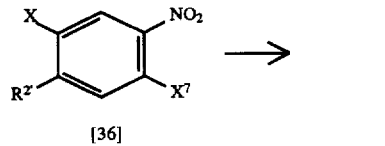

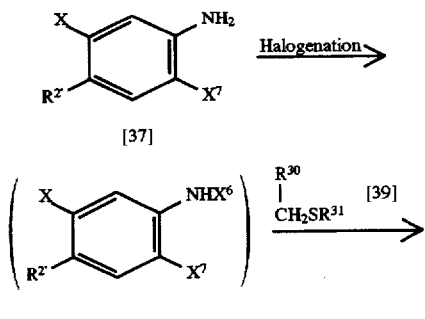

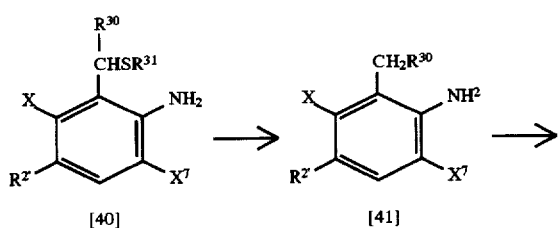

-continued
[Reaction scheme-X]

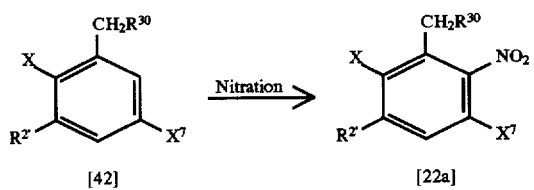

wherein $R^{2'}$, $X^6$ and $X^7$ are as defined above, $R^{30}$ is hydrogen atom or a (lower) alkyl, and $R^{31}$ is a (lower) alkyl, and $R^{30}$ and $R^{31}$ may combine together to form a 5- to 7-membered ring.

[Reaction scheme-XI]

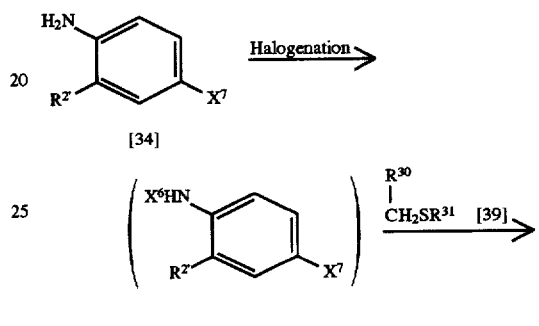

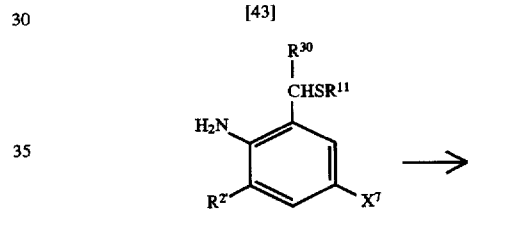

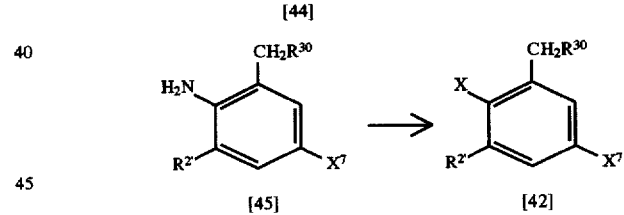

wherein $R^{2'}$, $X^6$, $X^7$, $R^{30}$ and $R^{31}$ are as defined above.

The nitration of each compound [32], [35] or [42] can be carried out under the same reaction conditions as employed in the nitration of the compound [28] or [29].

The reduction of the compound [33] or [36] is usually carried out by (i) reducing the compound with a catalyst for catalytic reduction in a suitable solvent, or by (ii) reducing the compound with a reducing agent such as a mixture of metal or metal salt with an acid or a mixture of metal or metal salt with hydroxide, sulfide or ammonium salt of alkali metal in a suitable innert solvent. In case of the process (i) of the catalytic reduction, the solvent employed in the reaction includes, for example, water, acetic acid, alcohols such as methanol, ethanol and isopropanol, hydrocarbons such as hexane and cyclohexane, ethers such as diethylene glycol dimethyl ether, dioxane, tetrahydrofuran and diethyl ether, esters such as ethyl acetate and methyl acetate, aprotic polar solvent such as N,N-dimethyl formamide, and the like. The catalyst for catalytic reduction employed in the reaction includes, for example, palladium, palladium black, palladium carbon, platinum, platinum oxide, copper chromite, Raney nickel, and the like. The catalyst is usually used in an amount of from 0.02 to 1.00 times weight based on the compound [33] or [36]. The reaction is usually carried out at a temperature of from around −20° C. to around 150° C., preferably from around 0° C. to room temperature at a hydrogen pressure of from 1 to 10 atm. for about 0.5 to about 10 hours. In case of using the process (ii), the employed reducing agent includes a mixture of iron, zinc, tin or tin (II) chloride with a mineral acid such as hydrochloric acid or sulfuric acid, a mixture of iron, iron (II) sulfate, zinc or tin with alkali metal hydroxide such as sodium hydroxide, sulfate such as ammonium sulfate, aqueous amminia or ammonium chloride, and the like. The innert solvent includes, for example, water, acetic acid, methanol, ethanol, dioxane and the like. The reaction conditions of the above reduction may vary depending on a kind of the reducing agent employed. For example, the reaction is advantageously carried out at a temperature of from around 0° C. to room temperature for about 0.5 to about 10 hours when the reducing agent is a combination of tin (II) chloride and hydrochloric acid. The reducing agent is usually employed in an amount of at least 1 mole, preferably 1 to 5 moles per 1 mole of the starting compound.

In case that $R^{30}$ and $R^{31}$ of the compound [40] or [44] are taken together to form a 5- to 7-membered ring, $R^{30}$ of the compound [41] or [45] is —$R^{30}$—$R^{31}$—H.

The compound [40] or [44] can be prepared by reacting the starting aniline derivative of the formula [37] or [34] with a halogenating agent and then reacting the resultant compound of the formula [38] or [43] with the thio compound of the formula [39].

The reaction between the aniline derivative [37] or [34] and the halogenating agent is usually carried out in a suitable solvent. The solvent may be any conventional solvents unless they give any undesirable effect on the reaction. Such solvent includes, for example, halogenated hydrocarbons such as chloroform and dichloromethane, ethers such as dioxane, diethyl ether and tetrahydrofuran, aromatic hydrocarbons such as benzene, toluene and xylene, lower alcohols such as methanol, ethanol and isopropanol, polar solvents such as DMSO, HMPA and acetonitrile, and the like. The halogenating agent employed in the above reaction may be any conventional halogenating agents and includes, for example, N-bromosuccinimide, N-chlorosuccinimide, sodium hypobromite, sodium hypochlorite, bleaching powder, thionyl chloride, tert-butyl hypochloride, and the like. The halogenating agent is usually used in an amount of at least 1 mole, preferably 1 to 6 moles, per 1 mole of the starting compound. The reaction is usually carried out at a temperature of from around −78° C. to room temperature, preferably from around −60° C. to around 15° C., and usually completes in a moment or within a few minutes.

By the reaction, there is produced the intermediate of the formula [38] or [43]. While the resultant compound [38] or [43] may be separated from the reaction mixture to provide it for a subsequent reaction, the reaction mixture is usually subjected to the reaction with the thio compound of the formula [39] without separating it from the reaction mixture.

The reaction between the intermediate compound [38] or [43] and the compound [39] is carried out in the same solvent and at the same temperature as mentioned above in the presence of a suitable basic compound. The preferable basic compound which can be employed in the reaction includes inorganic bases such as potassium carbonate, sodium carbonate, sodium hydroxide, sodium hydrogen carbonate, sodium amide and sodium hydride, and organic bases including tertiary amines such as triethylamine, tripropylamine, pyridine and quinoline. The compound [39] is usually used in an amount of at least 1 mole, preferably 1 to 1.5 moles, per 1 mole of the intermediate compound [38] or [43]. The reaction is usually carried out at a temperature of from room temperature to around 150° C., preferably from room temperature to around 100° C., for about 1 to about 50 hours.

The desulfurization of the compound [40] or [44] for preparing the compound [41] or [45] is usually carried out in a solvent in the presence of a suitable catalyst. The catalyst includes, for example, aluminum-amalgam, lithium-(lower) alkylamine, Raney nickel, Raney cobalt, triethyl phosphite, triphenyl phosphine, and the like, and preferably Raney nickel. The solvent includes alcohols such as methanol, ethanol and isopropanol, ethers such as diehtyl ether, dioxane and tetrahydrofuran, and the like. The reaction is usually carried out at a temperature of from around 0° C. to around 200° C., preferably from room temperature to around 100° C., for about 10 minutes to about 5 hours. The catalyst is usually used in an amount of from 1 to 10-fold by weight of the compound [40] or [44].

The reaction of converting the compound [34] or [45] into the compound [35] or [42] respectively is carried out by reacting the starting compound with nitrite of metal such as sodium nitrite or potassium nitrite in a solvent such as water in the presence of an acid to give a diazonium salt, which is then heated at from around 150° C. to around 200° C., or heated at from room temperature to around 150° C. in the presence of copper (I) bromide—hydrobromic acid, copper (I) chloride—hydrochloric acid, hydrobromic acid, potassium iodide, or an acid such as hydrochloric acid plus copper powder. The acid employed in the reaction includes, for example, hydrochloric acid, hydrobromic acid, sulfuric acid, tetrafluoroboric acid, hexafluorophosphoric acid, and the like. The acid and the nitrate of metal are usually used in an amount of from 1 to 5 moles, preferably from 1 to 3 moles, and of at least 1 mole, preferably from 1 to 1.5, moles, respectively, per 1 mole of the compound [34] or [45]. The amount of the acid employed in heating the obtained diazonium salt is usually at least 1 moles, preferably from 1 to 1.5 moles per 1 mole of the compound [34] or [46].

The deamination of the compound [41] to prepare the compound [42] is carried out by, for example, reacting the compound [41] with t-butyl nitrite in the presence of a suitable solvent. The solvent employed in the reaction includes, for example, dimethyl formamide, dimethyl sulfoxide, hexamethylphosphoric acid triamide, and the like. The t-butyl nitrite is usually used in an amount of at least 1 mole, preferably from 1 to 2 moles per 1 mole of the compound [41]. The reaction is usually carried out at a temperature of from room temperature to around 150° C., preferably from room temperature to around 100° C. for about 0.1 to 5 hours.

[Reaction scheme-XIII]

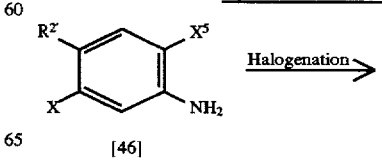

[46]

-continued
[Reaction scheme-XII]

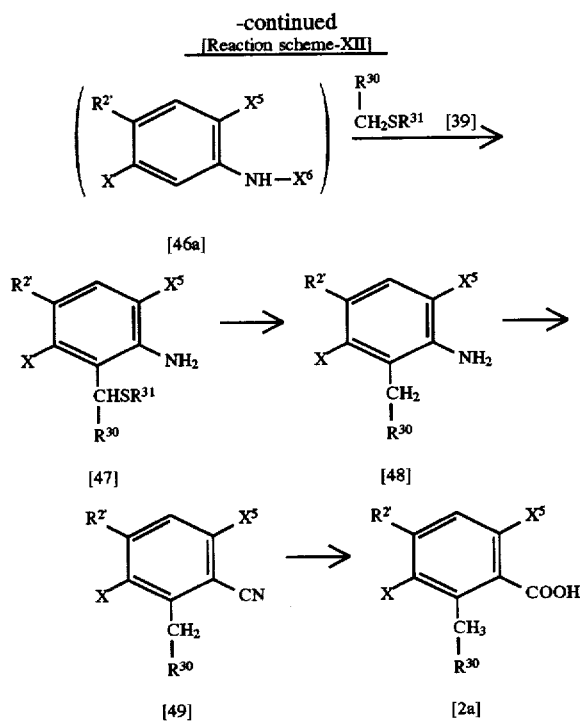

[Reaction scheme-XIII]

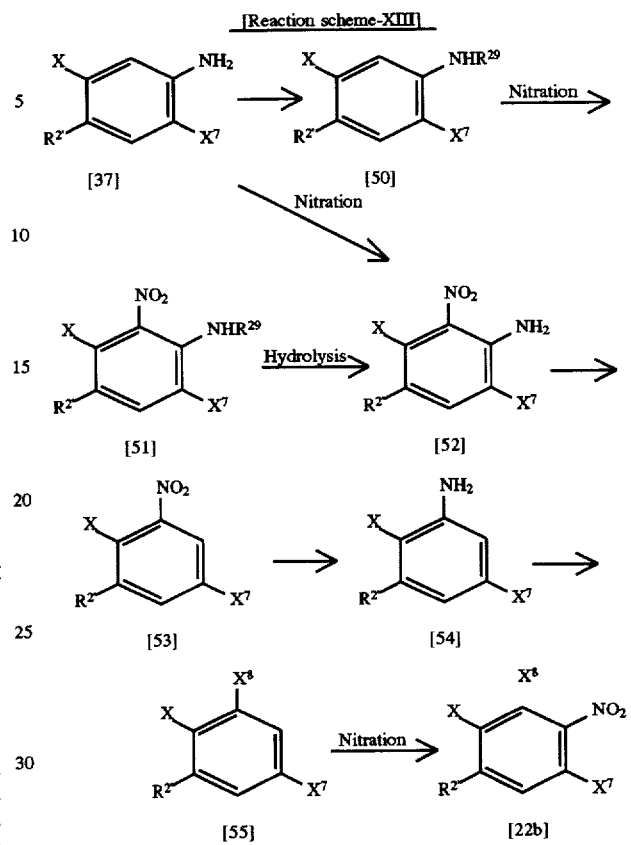

wherein $R^{2'}$, X, $X^5$, $X^6$, $R^{30}$ and $R^{31}$ are as defined above

The reaction between the compound [46] and the halogenating agent and the subsequent reaction with the compound [39] are carried out under the same reaction conditions as employed in the reaction between the above compound [37] or [34] and the halogenating agent and the subsequent reaction with the compound [39].

The desulfurization of the compound [47] to prepare the compound [48] is carried out under the same reaction conditions as employed in the desulfurization of the compound [40] or [44].

The reaction of converting the compound [48] into the compound [49] is carried out by treating the former compound under the same reaction conditions as employed in the reaction of converting the compound [34] or [45] into the diazonium salt to prepare diazonium salt, which is then reacted with MCN (wherein M is alkali metals such as sodium, potassium, etc. and metals such as silver, calcium, copper, etc.) in the presence of a copper compound such as copper powder or copper sulfate. The reaction is usually carried out at a temperature of from around 0° C. to around 100° C., preferably from around 0° C. to around 70° C. for about 0.5 to about 5 hours. The MCN is usually used in an amount of at least 1 mole, preferably 1 to 10 moles per 1 mole of the compound [48].

The hydrolysis of the compound [49] can be carried out in the presence of a suitable hydrolysis catalyst, including inorganic acids such as hydrohalogenic acids (e.g. hydrochloric acid, hydrobromic acid, etc.), mineral acids (e.g. sulfuric acid, phosphoric acid, etc.), and inorganic alkaline compounds such as alkali metal hydroxides (e.g. sodium hydroxide, potassium hydroxide, etc.), alkali metal carbonates or bicarbonates (e.g. sodium carbonate, potassium carbonate, sodium hydrogen carbonate, etc.), in the presence or absence of a solvent (e.g. water, or a mixture of water and a lower alcohol such as methanol, ethanol, etc.). The reaction is usually carried out at a temperature of from 50° C. to 200° C., preferably from 70° C. to 180° C. for about 1 to 10 hours.

wherein $R^{2'}$, X, $X^7$, and $R^{29}$ are as defined above and $X^8$ is a halogen atom.

The reaction of converting the compound [37] into the compound [50] can be carried out under the same reaction conditions as employed in the above reaction of converting the compound [28] into the compound [29].

The nitration of the compound [37], [50] or [55] can be carried out under the same reaction conditions as employed in the above nitration of the compound [28] or [29].

The hydrolysis of the compound [51] can be carried out under the same reaction conditions as employed in the above hydrolysis of the compound [1a].

The deamination of the compound [52] to prepare the compound [53] can be carried out under the same reaction conditions as employed in the above deamination of the compound [41].

The reduction of the compound [53] can be carried out in the same reaction conditions as employed in the above reduction of the compound [33] or [36].

The reaction of converting the compound [54] into the compound [55] can be carried out in the same manner as in the above reaction of converting the compound [34] or [45] into the compound [35] or [42].

The compounds [3], [5], [7], [9], [1a], [1a'], [1b'], [23], [25] and [26], wherein $R^2$ is a saturated or unsaturated 5- to 9-membered heterocyclic ring having a substituent of oxo, can be reduced to the corresponding compounds, wherein $R^2$ is a saturated or unsaturated 5- to 9-membered heterocyclic ring having a substituent of hydroxy. The reduction can be carried out with a hydrogenating reducing agent in the presence of a suitable solvent. The reducing agent includes, for example, sodium borohydride, lithium aluminum hydride, diborane and the like. The reducing agent is usually used in an amount of at least 1 mole, preferably 1 to 5 moles per 1 mole of the starting material to be reduced. The solvent includes, for example, water, a (lower) alcohol such as methanol, ethanol or isopropanol, an ether such as tetrahydrofuran, diethyl ether or diglyme, and the like. The reaction is usually carried out at a temperature of from around −60° C. to 50° C., preferably from around −30° C. to room temperature for about 10 minutes to about 5 hours. In case of using lithium aluminum hydride or diborane as the reducing agent, non-aqueous solvent is preferably employed such as diethyl ether, tetrahydrofuran or diglyme.

In case of using sodium borohydride as the reducing agent, an inorganic base such as sodium hydroxide can also be added to the reaction system.

The compounds wherein $R^2$ is a saturated or unsaturated 5- to 9-membered heterocyclic ring having a substituent selected from the group consisting of a (lower) alkyl having at least 1 of a (lower) alkanoylamino and a (lower) alkoxycarbonylamino, a (lower) alkanoylamino and a (lower) alkoxycarbonylamino can be hydrolized into the corresponding compounds wherein $R^2$ is a saturated or unsaturated 5- to 9-membered heterocyclic ring having a substituent selected from the group consisting of a (lower) alkyl having at least one amino and amino. The hydrolysis can be carried out under the same reaction conditions as employed in the hydrolysis of the compound [1a] in the above reaction scheme-I.

The compounds wherein $R^2$ is a saturated or unsaturated 5- to 9-membered heterocyclic ring having at least one —NH— in the ring can be converted into the compounds wherein $R^2$ is a saturated or unsaturated 5- to 9-membered heterocyclic ring substituted by at least one (lower) alkanoyl, by reacting the former compounds under the same reaction conditions as employed in the reaction of converting the compound [28] into the compound [29] in the above reaction scheme-IX.

The compounds [3], [5], [7], [9], [1a], [1a'], [1b], [1b'], [23], [25]and [26] wherein $R^1$ is a phenyl having at least one (lower) alkoxy on the phenyl ring can be converted into the corresponding compounds wherein $R^1$ is a phenyl having at least one hydroxy on the phenyl ring, by heating the former compounds in an aqueous hydrobromic acid solution.

The compound [1] wherein $R^3$ is a halogen atom can be converted into the corresponding compound [1] wherein $R^3$ is hydroxy, by treating the former compound in water and a basic compound such as sodium hydroxide, potassium hydroxide or barium hydroxide at from room temperature to around 200° C., preferably from room temperature to around 150° C. for about 1 to 15 hours.

[Reaction scheme-XIV]

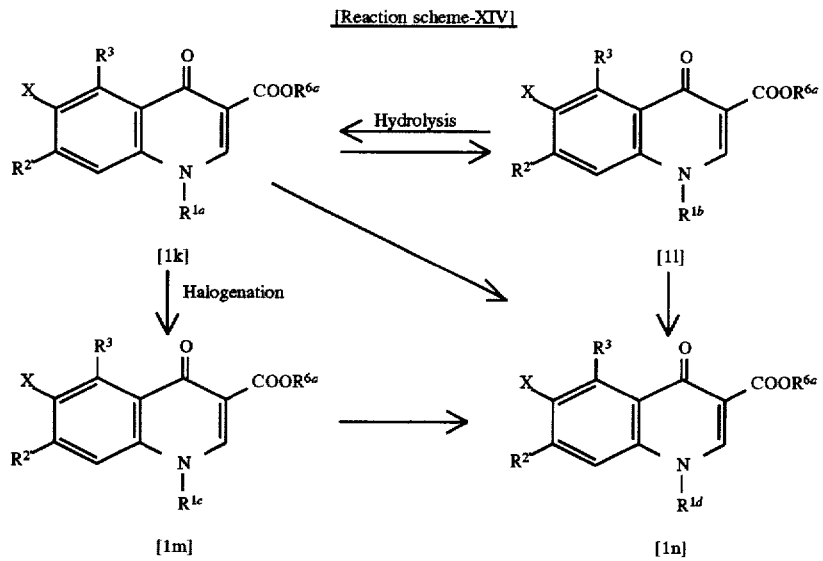

wherein $R^{2'}$, $R^3$ and X are as defined above, and $R^{6a}$ is hydrogen atom or a (lower) alkyl, $R^{1a}$ is a (lower) alkyl having 1 to 3 of hydroxy, $R^{1b}$ is a (lower) alkyl having 1 to 3 of a (lower) alkanoyloxy, $R^{1c}$ is a (lower) alkyl having 1 to 3 of halogen atoms and $R^{1d}$ is a (lower) alkenyl.

The reaction of converting the compound [1k] into the compound [1l] can be carried out under the same reaction conditions as employed in the above reaction of converting the compound [28] into the compound [29].

The hydrolysis of the compound [1l] can be carried out under the same reaction conditions as employed in the above hydrolysis of the compound [1a].

The halogenation of the compound [1k] can be carried out under the same reaction conditions as employed in the above halogenation of the compound [2].

The reaction of converting the compound [1k] into the compound [1n] is carried out in a suitable solvent or without a solvent in the presence of a hydrohalogenic acid such as hydochloric acid or hydrobromic acid, an inorganic acid such as sulfuric acid, boric acid or potassium hydrogensulfate, or an organic acid such as oxalic acid. The solvent employed in the reaction includes, for example, water, an ether such as dioxane, tetrahydrofuran or diethyl ether, a halogenated hydrocarbon such as dichloromethane, chloroform or carbon tetrachloride, an aromatic hydrocarbon such as benzene, toluene or xylene, or a mixture thereof. The reaction is usually carried out at a temperature of from around 50° C. to around 350° C., preferably from around 80° C. to around 300° C. for about 10 minutes to about 10 hours.

The reaction of converting the compound [1z] into the compound [1n] is carried out in a suitable solvent or without a solvent. The solvent employed in the reaction may be any which is exemplified in the above reaction of converting the compound [1k] into the compound [1n]. The reaction is usually carried out at a temperature of from room temperature to around 150° C., preferably from room temperature to around 100° C. for about 10 minutes to about 10 hours. The reaction may also be conducted in the presence of an inorganic base such as sodium carbonate, potassium carbonate, sodium hydrogen carbonate, potassium hydrogen carbonate, sodium hydroxide, potassium hydroxide, lithium salt such as lithium chloride or lithium carbonate, or an organic base such as DBU, pyridine, triethanol amine or triethyl amine.

The reaction of converting the compound [1m] into the compound [1n] is carried out in a suitable solvent in the presence of a basic compound. The solvent and the basic compound employed in the reaction may be any which is exemplified in the above reaction of converting the compound [1l] into the compound [1n]. The reaction is usually carried out at a temperature of from room temperature to around 200° C., preferably from room temperature to around 150° C. for about 1 to about 10 hours.

The compounds [1k], [1l], [1m] and [1n] wherein $R^{6a}$ is a (lower) alkyl can be converted into the corresponding compounds wherein $R^{6a}$ is hydrogen atom, by hydrolyzing the former compounds under the same reaction conditions as employed in the above hydrolysis of the compound [1a].

In the hydrolysis of the compound [14] wherein $R^{6a}$ is a (lower) alkyl, $R^{6a}$ is also hydrolyzed in some cases to give the compound [1l] wherein $R^{6a}$ is hydrogen atom, which can easily be separated from the reaction mixture.

In the halogenation of the compound [1k] wherein $R^{6a}$ is hydrogen atom, the carboxy in the compound is also halogenated in some cases but this one can be easily separated from the reaction mixture.

[Reaction scheme-XV]

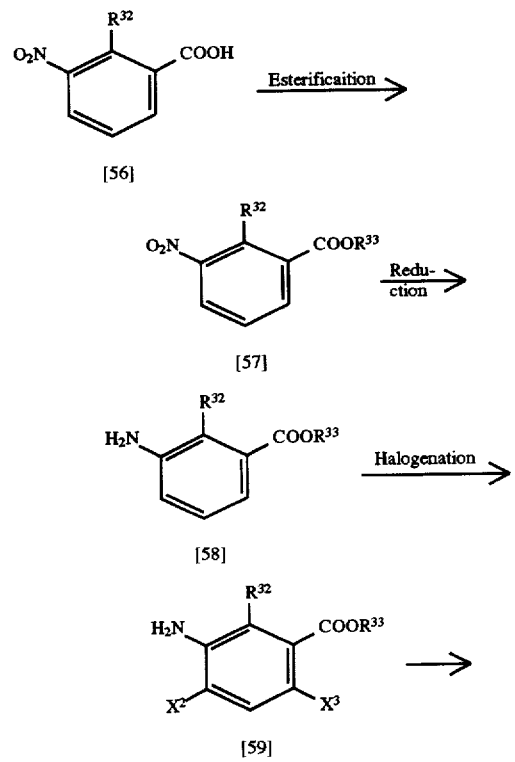

[56]

[57]

[58]

[59]

-continued
[Reaction scheme-XV]

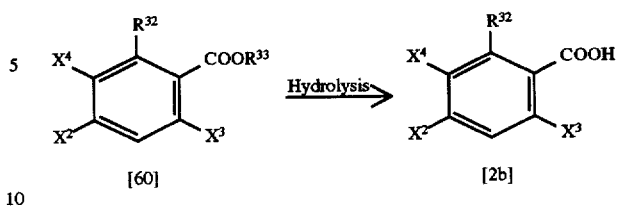

[60]    [2b]

Wherein $X^2$, $X^3$ and $X^4$ are as defined above, $R^{32}$ and $R^{33}$ each are a (lower) alkyl.

The eserification of the compound [56] is carried out in a (lower) alcohol such as methanol, ethanol or isopropanol in the presence of a halogenating agent such as an acid such as hydrochloric acid or sulfuric acid, thionyl chloride, phosphorus oxychloride, phosphorus pentachloride or phosphorus trichloride. The reaction is usually carried out at a temperature of from around 0° C. to 150° C., preferably from around 50° C. to around 100° C. for about 1 to 10 hours.

The reduction of the compound [57] can be carried out under the same reaction conditions as employed in the above reduction of the compound [33] or [36].

The halogenation of the compound [58] is carried out in a suitable solvent in the presence of a halogenating agent. The halogenating agent employed in the reaction includes a halogen such as bromine or chlorine, iodine chloride, sulufuryl chloride, N-halogenosuccinimide such as N-bromosuccinimide or N-chlorosuccinimide. The halogenating agent is usually used in an amount of from 1 to 10 moles, preferably from 1 to 5 moles per 1 mole of the compound [58]. The solvent includes a halogenated hydrocarbon such as dichloromethane, dichloroethane, chloroform or carbon tetrachloride, a (lower) alkanoic acid such as acetic acid or propionic acid, water and the like. The reaction is usually carried out at a temperature of from around 0° C. to around the boiling point of the solvent, preferably from around 0° C. to around 40° C. for about 0.1 to about 10 hours.

The reaction of converting the compound [59] into the compound [60] can be carried out under the same reaction conditions as employed in the above reaction of converting the compound [34] or [45] into the compound [35] or [42].

The hydrolysis of the compound [60] can be carried out under the same reaction conditions as employed in the above hydrolysis of the compound [1a].

The compounds [1a] in the reaction scheme-I and the compounds [1b] and [1b'] in the reaction scheme-II are useful not only as an intermediate for preparing the compound [1] of the present invention with antimicrobial activities, but also as an antimicrobial agent because they also have antimicrobial activities.

The compound [1] of the present invention can easily be converted into a salt thereof by treaing with a pharmaceutically acceptable acid or base. The acid includes inorganic acids such as hydrochloric acid, sulfuric acid, phosphoric acid and hydrobromic acid and organic acids such as oxalic acid, maleic acid, fumaric acid, malic acid, tartaric acid, citric acid, benzoic acid, lactic acid, methanesulfonic acid and propionic acid. The base includes sodium hydroxide, potassium hydroxide, calcium hydroxide, sodium carbonate, potassium hydrogen carbonate, and the like.

The compound thus obtained can easily be isolated and purified by conventional methods, such as, for example, extraction with solvents, dilution method, recrystallization, column chromatography and preparative thin layer chromatography.

The compound [1] of the present invention or salts thereof show an excellent antimicrobial activity against mycoplasma, *Pseudomonas aeruginosa*, anaerobic bacteria, resistant cells against various antimicrobials, clinically isolated bacteria, and gram negative and gram positive bacteria such as *Enterococcus faecalis* and *Staphylococcus pyogenes* and hence are useful as an antimicrobial agent for the treatment of diseases induced by these microorganisms. These compounds also show low toxicity and less side effect and are characteristic in good absorbability and in sustained activity. Moreover, the compounds are highly excreted via urine and hence are useful for the treatment of urinary infectious diseases, and further because of easy excretion via bile, they are also useful for the treatment of intestinal infectious diseases.

Among the compounds [1] of the present invention, the preferable ones are the compounds wherein $R^1$ is unsubstituted cyclopropyl, X is chlorine or fluorine atom, most preferably fluorine atom, $R^4$ is a (lower) alkyl such as, preferably methyl or ethyl, most preferably methyl, and $R^3$ is hydrogen atom, a (lower) alkyl or a halogen atom, most preferably hydrogen atom, with a (lower) alkyl being preferably methyl or ethyl, most preferably methyl, and a halogen atom being preferably chlorine atom or fluorine atom, most preferably fluorine atom.

The absorbability of the compounds of the present invention in the living body can be increased by converting them into the corresponding salt such as, for example, lactate or hydrochloride.

The compounds of the present invention are usually used in the form of a usual pharmaceutical preparation. The pharmaceutical preparation can be prepared in admixture with conventional pharmaceutically acceptable diluents or carriers, such as fillers, bulking agents, binding agents, wetting agents, disintegrators, surfactants and lubricating agents. The pharmaceutical preparation includes various preparations suitable for treatment of the diseases, for example, tablets, pills, powders, solutions, suspensions, emulsions, granules, capsules, suppositories, injections such as solutions and suspensions, and the like. In the preparation of tablets, there may be used any conventional carriers, for example, excepients such as lactose, white sugar, sodium chloride, glucose, urea, starches, calcium carbonate, kaolin, crystalline cellulose and silicate, binding agents such as water, ethanol, propanol, simple syrup, glucose solution, starch solution, gelatin solution, carboxymethyl cellulose, shellac, methyl cellulose, potassium phosphate and polyvinylpyrrolidone, disintegrators such as dry starch, sodium alginate, agar powder, laminaran powder, sodium hydrogen carbonate, calcium carbonate, polyoxyethylene sorbitan fatty acid esters, sodium laurylsulfate, stearic monoglyceride, starches and lactose, disintegration inhibitors such as white sugar, stearin, cacao butter and hydrogenated oils, absorption promoters such as quaternary ammonium salts and sodium laurylsulfate, wetting agents such as glycerin and starches, adsorbents such as starches, lactose, kaolin, bentonite and colloidal silicates, rublicants such as purified talc, stearates, boric acid powder and polyethylene glycol, and the like. The tablets may also be coated with conventional coating agents, for example, may be in the form of a sugar coated tablet, a gelatin-coated tablets, an enteric coating tablet, a film coating tablet, or a double or multiple layers tablet. In the preparation of pills, there may be used conventional carries, including excipients such as glucose, lactose, starches, cacao butter, hydrogenated vegetable oils, kaolin and talc, binding agents such as gum arabic powder, tragacanth powder, gelatin and ethanol, disintegrators such as laminaran and agar, and the like. In the preparation of suppositories, there may be used conventional carriers, such as, for example, polyethylene glycol, cacao butter, higher alcohols, higher alcohol esters, gelatin and semi-synthetized glycerides. In the preparation of injections, the solutions, emulsions or suspensions of the compounds are sterilized and are preferably made isotonic with the body liquid. These solutions, emulsions and suspensions are prepared by admixing the active compound with a conventional diluent, such as water, aqueous lactic acid solution, ethyl alcohol, propylene glycol, ethoxylated isostearyl alcohol, polyoxylated isostearyl alcohol or polyoxyethylene sorbitan fatty acid esters. The preparations may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, preservatives, perfumes, flavors, sweetening agents, and other medicaments. The preparations in the form of a paste, cream or gel may be prepared by using as a diluent white vaseline, paraffin, glycerin, cellulose derivatives, polyethylene glycol, silicone, bentonite, or the like. When the compound of the active ingredient precipitates in the injection, an acid such as, for example, methanesulfonic acid, propionic acid, hydrochloric acid, succinic acid or lactic acid may be added to the injection as required to preserve the injection in a stable solution.

The pharmaceutical preparation of the present invention may also be in the form of an infusable or injectable solution containing the above compound [1] or a salt thereof such as lactate and an acid not producing a precipitate. The acid not producing a precipitate includes, for example, lactic acid, methanesulfonic acid, propionic acid, hydrochloric acid, succinic acid, and the like, preferably lactic acid. In case of using lactic acid, the acid is usually used in an amount of from around 0.1 to around 10% by weight, preferably from around 0.5 to around 2% by weight, based on the weight of the above infusable or injectable solution. In case of using an acid other than lactic acid, the acid is usually used in an amount of from around 0.05 to around 4% by weight, preferably from around 0.3 to around 2% by weight, based on the weight of the above solution. The above infusable or injectable solution may optionally be added with conventional additives, which includes, for example, a thickener, an absorption promoter or inhibitor, a crystallization inhibitor, a complex-forming agent, an antioxidant, an isotonicity-giving agent, or a hydrating agent, and the like. The pH of the solution can properly be adjusted by adding an alkali such as sodium hydroxide, and is usually adjusted within the range of from 2.5 to 7. The infusable or injectable solution thus prepared has an excellent stability, and can be stored and preserved for a long time with retaining the solution state.

The active compounds [1] or salts thereof may be contained in any amount in the preparations, and are usually contained in an amount of from 1 to 70% by weight based on the whole weight of the preparations.

The pharmaceutical preparations of the present invention can be administered in any methods. Suitable method for administration may be selected in accordance with the preparation form, age and sex of patients, severity of the diseases, and the like. For instance, tablets, pills, solutions, suspensions, emulsions, granules and capsules are administered in oral route. In case of injection, it is administered intravenously in a single form or together with an auxiliary liquid such as glucose or amino acid solution. The injections may also be administered in intramuscular, intracutaneous, subcutaneous, or intraperitoneal route. Suppositories are administered in intra-rectal route.

The dosage of the pharmaceutical preparations of the present invention may vary according to administration methods, age and sex of patients, severity of the diseases, and the like, usually in the range of about 0.2 to about 100 mg of the active compound [1] or a salt thereof per 1 kg body weight of the patient per day. The preparation is usually administered by dividing into 2 to 4 times per day.

The present invention is illustrated by the following Reference Examples, Examples, Experiments and Preparations. It is to be understood that the present invention is not limited to these Examples or Experiments and various changes and modifications can be made without departing from the scope and spirit of the present invention.

REFERENCE EXAMPLE 1

To 2,4,5-trifluoroaniline (35.0 g) are added anhydrous dichloromethane (530 ml) and dimethyl sulfide (24.6 ml) and the mixture is cooled to 0° C. Thereto N-chlorosuccinimide (38.2 g) is gradually added below 5° C. After the mixture is stirred at the same temperature for 15 minutes, triethylamine (47.7 ml) is gradually added. After reflux for 12 hours, the resultant is made alkaline with 5% aqueous sodium hydroxide solution, extracted with dichloromethane, and the extract is dried over sodium sulfate and concentrated. The residue is purified with column chlomatography (silica-gel, dichloromethane: n-hexane= 1:4) to give 2-methylthiomethyl-3,4,6-trifluoroaniline (22.3 g).

$^1$H-NMR (CDCl$_3$) δ ppm: 2.03 (3H, s), 3.76 (2H, d, J=1.5 Hz), 4.03 (2H, brs), 6.48 (1H, dt, J=7.2 Hz, 10.1 Hz)

REFERENCE EXAMPLE 2

To 2-methylthiomethyl-3,4,6-trifluoroaniline (22.2 g) are added ethanol (400 ml) and Raney nickel (200 g) and the mixture is stirred at room temperature for 30 minutes. After the catalyst is filtered off, the filtrate is added with water and extracted with dichloromethane. The is dried over magnesium sulfate and concentrated to give 2-methyl-3,4,6-trifluoroaniline (12.3 g).

$^1$H-NMR (CDCl$_3$) δ ppm: 2.13 (3H, d, J=2.1 Hz), 3.56 (2H, brs), 6.75 (1H, dt, J=7.2 Hz, 10.2 Hz)

REFERENCE EXAMPLE 3

To 2-methyl-3,4,6-trifluoroaniline (10.6 g) is added a mixture of conc. sulfuric acid (13.8 ml) and water (46 ml) and the mixture is cooled. Thereto an aqueous solution (20 ml) of sodium nitrite (5.5 g) is added dropwise at 0°–5° C. The solution is gradually added to a mixture of copper (II) sulfate 5 hydrate (41 g), potassium cyanide (43 g), ammonium hydroxide (60 ml) and water (260 ml) at 10°–30° C. The mixture is extracted with dichloromethane and the extract is dried over sodium sulfate, concentrated and the residue is purified with column chromatography (silica-gel, dichloromethane:n-hexane=1:4) to give 2-methyl-3,4,6-trifluorobenzonitrile (4.3 g).

$^1$H-NMR (CDCl$_3$) δ ppm: 2.52 (3H, d, J=2.5 Hz), 6.94 (1H, dt, J=6.2 Hz, 8.9 Hz)

REFERENCE EXAMPLE 4

To 2-methyl-3,4,6-trifluorobenzonitrile (4.3 g) is added 50% sulfuric acid (40 ml) and the mixture is heated at 150°–160° C. for 6 hours. After cooling, the mixture is poured into ice-water and extracted with diethyl ether. The ether layer is added with water and made alkaline with 5% aqueous sodium hydroxide solution while the water layer is made acidic with conc. hydrochloric acid. The resultant is subjected to extraction with diethyl ether, and the extract is dried over magnesium sulfate and concentrated to give 2-methyl-3,4,6-trifluorobenzoic acid (3.3 g).

$^1$H-NMR (CDCl$_3$) δ ppm: 2.47 (3H, d, J=2.6 Hz), 6.88 (1H, dt, J=6.3 Hz, 9.5 Hz)

REFERENCE EXAMPLE 5

To 2-methyl-3,4,6-trifluorobenzoic acid (3.2 g) is added thiony chloride (7 ml) and the mixture is refluxed for 1 hour. After concentrating, 2-methyl-3,4,6-trifluorobenzoyl chloride (3.3 g) is obtained.

Separately, two drops of carbon tetrachloride are added to a solution of metallic magnesium (0.4 g) in absolute ethanol (0.9 ml). When the reaction starts, a mixture of diethyl malonate (2.6 ml), absolute ethanol (1.6 ml) and anhydrous toluene (6 ml) is added dropwise below 60° C. After stirring at 60° C. for 1 hour, the reaction mixture is cooled to 0° C. and thereto a solution of 2-methyl-3,4,6-trifluorobenzoyl chloride prepared above in toluene (5 ml) is added dropwise. After stirring for 30 minutes, a mixture of conc. sulfuric acid (0.4 ml) and water (6 ml) is added and the mixture is extracted with diethyl ether, and the extract is dried over magnesium sulfate and concentrated to give diethyl 2-methyl-3,4,6-trifluorobenzoylmalonate (5.2 g).

REFERENCE EXAMPLE 6

To diethyl 2-methyl-3,4,6-trifluorobenzoylmalonate (5.1 g) are added water (20 ml) and p-toluenesulfonic acid (30 mg) and the mixture is refluxed for 2.5 hours. After cooling, the resultant is extracted with diethyl ether, and the extract is dried over magnesium sulfate and concentrated to give ethyl 2-methyl-3,4,6-trifluorobenzoylacetate (3.3 g).

REFERENCE EXAMPLE 7

To ethyl 2-methyl-3,4,6-trifluorobenzoylacetate (3.2 g) are added acetic anhydride (3.0 g) and triethoxymethane (2.7 g) and the mixture is refluxed for 1 hour. After concentrating, ethyl 2-(2-methyl-3,4,6-trifluorobenzoyl)-3-ethoxyacrylate (3.5 g) is obtained.

REFERENCE EXAMPLE 8

Ethyl 2-(2-methyl-3,4,6-trifluorobenzoyl)-3-ethoxyacrylate (3.5 g) is dissolved in ethanol (25 ml) and thereto cyclopropylamine (0.84 ml) is added dropwise under ice-cooling. After stirring at room temperature for 30 minutes, the mixture is concentrated and the residue is purified with column chromatography (silica-gel, dichloromethane: n-hexane =1: 1) to give ethyl 2-(2-methyl-3,4, 6-trifluorobenzoyl)-3-cyclopropylaminoacrylate (2.7 g).

REFERENCE EXAMPLE 9

Ethyl 2-(2-methyl-3,4,6-trifluorobenzoyl)-3-cyclopropylaminoacrylate (2.6 g) is dissolved in anhydrous dioxane (26 ml) and thereto 60% sodium hydride (0.38 g) is gradully added under ice-cooling. After stirring at room temperature for 30 minutes, the reaction mixture is poured into ice-water and extracted with dichloromethane. The extract is dried over magnesium sulfate and concentrated. The residue is added with diethyl ether and crystals are filtered, which are recrystalized from ethanol to give ethyl 1-cyclopropyl-6,7-difluoro-5-methyl-1,4-dihydro-4-oxoquinoline-3-carboxylate (2.0 g). m.p. 185°–187° C.

REFERENCE EXAMPLE 10

To ethyl 1-cyclopropyl-6,7-difluoro-5-methyl-1,4-dihydro-4-oxoquinoline-3-carboxylate (1.9 g) are added 90% acetic acid (20 ml) and conc. hydrochloric acid (5 ml) and the mixture is refluxed for 2 hours. After cooling, the precipitated crystals are isolated, washed with water, ethanol, and diethyl ether in this order to give 1-cyclopropyl-6,7-difluoro-5-methyl-1,4,-dihydro-4-oxoquinoline-3-carboxylic acid (1.6 g), as colorless needles, m.p. 294°–298° C.

$^1$H-NMR (CF$_3$COOD) δ ppm: 1.43–1.55 (2H, m), 1.65–1.81 (2H, m), 3.06 (3H, d, J=2.8 Hz), 4.08–4.20 (1H, m), 8.40 (1H, dd, J=6.8 Hz, 10.3 Hz), 9.46 (1H,s)

REFERENCE EXAMPLE 11

Employing ethyl 2-(2-methyl-3,4,6-trifluorobenzoyl)-3-ethoxyacrylate (1.0 g) and p-fluoroaniline (0.39 g), the procedure of Reference Example 8 is repeated to give ethyl 2-(2-methyl-3,4,6-trifluorobenzoyl)-3-(4-fluorophenyl) aminoacrylate, which is then treated with 60% sodium hydride (0.15 g) as in Reference Example 9 to give ethyl 1-(4-fluorophenyl)-5-methyl-6,7-difluoro-1,4-dihydro-4-oxoquinoline-3-carboxylate (0.64 g), as white crystals (recrystallized from ethanol), m.p. 256°–259° C.

REFERENCE EXAMPLE 12

Employing ethyl 1-(4-fluorophenyl)-5-methyl-6,7-difluoro-1,4-dihydro-4-oxoquinoline-3-carboxylate (0.56 g), conc. hydrochloric acid (1.5 ml), and 90% acetic acid (6 ml), the procedure of Reference Example 10 is repeated to give 1-(4-fluorophenyl)-5-methyl-6,7-difluoro-1,4-dihydro-4-oxoquinoline-3-carboxylic acid (0.49 g), as white crystals, m.p. 255°–257° C.

REFERENCE EXAMPLE 13

Employing ethyl 2-(2-methyl-3,4,6-trifluorobenzoyl)-3-ethoxyacrylate (1.0 g) and 70% aqueous ethylamine solution (0.24 ml), the procedure of Reference Example 8 is repeated to give ethyl 2-(2-methyl-3,4,6-trifluorobenzoyl)-3-ethylaminoacrylate, which is then treated with 60 % sodium hydride (0.15 g) as in Reference Example 9 to give ethyl 1-ethyl-5-methyl-6,7-difluoro-1,4-dihydro-4-oxoquinoline-3-carboxylate (0.6 g), as white crystals, m.p. 157°–159° C.

REFERENCE EXAMPLE 14

Employing ethyl 1-ethyl-5-methyl-6,7-difluoro-1,4-dihydro-4-oxoquinoline-3-carboxylate (0.55 g), conc. hydrochloric acid (1.5 ml) and 90% acetic acid (6 ml), the procedure of Reference Example 10 is repeated to give 1-ethyl-5-methyl-6,7-difluoro-1,4-dihydro-4-oxoquinoline-3- carboxylic acid (0.40 g), as white crystals, m.p. >300° C.

$^1$H-NMR (DMSO-d$_6$) δ ppm: 1.37 (3H, t, J=7.2 Hz), 2.82 (3H, d, J=3.2 Hz), 4.54 (2H, q, J=7.2 Hz), 8.07 (1H, dd, J=7.2 Hz, 9.8 Hz), 9.00 (1H, s), 15.25 (1H, s)

REFERENCE EXAMPLE 15

To 2-methyl-3-nitrobenzoic acid (10.0 g) is added methanol (100 ml) and thereto thionyl chloride (8 ml) is added dropwise at room temperature. After reflux for 2 hours, the reaction mixture is poured into ice-water and extracted with dichloromethane. The solvent is concentrated to give methyl 2-methyl-3-nitrobenzoate (10.8 g).

$^1$H NMR (CDCl$_3$) δ:2.63 (3H, s), 3.94 (3H, s), 7.38 (1H, t, J=8 Hz), 7.84 (1H, d, J=8 Hz), 7.99 (1H, d, J=8 Hz)

REFERENCE EXAMPLE 16

Methyl 2-methyl-3-nitrobenzoate (10.0 g) is dissolved in acetic acid (50 ml) and thereto 5% Pd-C (1 g) is added to carry out catalytic reduction at room temperature under 1 atm. After 1.5 hours, the catalyst is filtered off. The reaction mixture is concentrated, and thereto is added water, and the mixture is made alkaline with potassium carbonate, followed by extraction with dichloromethane. The solvent is concentrated to give methyl 2-methyl-3-aminobenzoate (8.6 g).

$^1$H-NMR (CDCl$_3$) δ ppm: 2.34 (3H, s), 3.55–3.85 (2H, brs), 3.87 (3H, s), 6.80 (1H, d, J=8 Hz), 7.04 (1H, t, J=8 Hz), 7.20 (1H, d, J=8 Hz)

REFERENCE EXAMPLE 17

To methyl 2-methyl-3-aminobenzoate (1.6 g) are added acetic acid (20 ml) and sodium acetate (1.6 g). Thereto a solution of bromine (3.1 g) in acetic acid (5 ml) is added dropwise below 20° C. over a period of 10 minutes. After the mixture is stirred at room temperature for 30 minutes, the reaction mixture is poured into ice-water and the resultant is extracted with diethyl ether. The ether layer is neutralized with potassium carbonate and dried. The solvent is concentrated to give methyl 2-methyl-3-amino- 4,6-dibromobenzoate (2.8 g).

$^1$H NMR (CDCl$_3$) δ:2.14 (3H, s), 3.93 (3H, s), 4.05–4.30 (2H, brs), 7.52 (1H, s)

REFERENCE EXAMPLE 18

To methyl 2-methyl-3-amino-4,6-dibromobenzoate (1.4 g) are added ethanol (5 ml) and 42% tetrafluoroboric acid (2.5 ml), and thereto is added dropwise a solution of sodium nitrite (0.33 g) in water (1 ml) below 5° C. After stirring the mixture for 10 minutes, the precipitated crystals are filtered and washed with a small amount of water, ethanol and diethyl ether in this order to give methyl 2-methyl-4,6-dibromo-3-benzoate diazonium tetrafluoroborate (1.6 g), m.p. 202°–204° C. (dec.).

REFERENCE EXAMPLE 19

Methyl 2-methyl-4,6-dibromo-3-benzoate diazonium tetrafluoroborate (1.3 g) is heated at 200° C. for 10 minutes. After cooling, the reaction mixture is added with ice-water and extracted with dichloromethane. The solvent is concentrated and the obtained residue is purified by silica-gel column-chromatography (eluent; chloroform: n-hexane= 1:4) to give methyl 2-methyl-3-fluoro-4,6-dibromobenzoate (0.6 g).

$^1$H NMR (CDCl$_3$) δ:2.27 (3H, d, J=2.5 Hz), 3.95 (3H, s), 7.63 (1H, d, J=5.8 Hz)

REFERENCE EXAMPLE 20

To methyl 2-methyl-3-fluoro-4,6-dibromobenzoate (75.5 g) are added ethanol (460 ml) and 10% aqueous solution of sodium hydroxide (460 ml) and the mixture is refluxed for 2 hours. After cooling, the reaction mixture is diluted with water and extracted with diethyl ether. The aqueous layer is made acidic with conc. hydrochloric acid and extracted with diethyl ether. The solvent is concentrated to give 2-methyl-3-fluoro-4,6-dibromobenzoic acid (61 g), m.p. 144°–146° C.

REFERENCE EXAMPLE 21

Employing 4,6-dibromo-3-fluoro-2-methylbenzoic acid (2.0 g), the procedure of Reference Example 5 is repeated to give 4,6-dibromo-3-fluoro-2-methylbenzoyl chloride (2.0 g).

$^1$H-NMR (CDCl$_3$) δ ppm: 2.37 (3H, d, J=2.5 Hz), 7.69 (1H, d, J=5.8 Hz)

REFERENCE EXAMPLE 22

Employing diethyl 4,6-dibromo-3-fluoro-2-methylbenzoyl chloride (2.0 g), the procedure of Reference Example 5 is repeated to give diethyl 4,6-dibromo-3-fluoro-2-methylbenzoylmalonate (2.6 g).

REFERENCE EXAMPLE 23

Employing diethyl 4,6-dibromo-3-fluoro-2-methylbenzoylmalonate (2.6 g), the procedure of Reference Example 6 is repeated to give ethyl 4,6-dibromo-3-fluoro-2-methylbenzoylacetate (2.1 g).

REFERENCE EXAMPLE 24

Employing ethyl 4,6-dibromo-3-fluoro-2-methylbenzoylacetate (2.1 g), the procedure of Reference Example 7 is repeated to give ethyl 2-(4,6-dibromo-3-fluoro-2-methylbenzoyl)-3-ethoxyacrylate (2.1 g).

REFERENCE EXAMPLE 25

Employing ethyl 2-(4,6-dibromo-3-fluoro-2-methylbenzoyl)-3-ethoxyacrylate (69.5 g), the procedure of Reference Example 8 is repeated to give ethyl 2-(4,6-dibromo-3-fluoro-2-methylbenzoyl)-3-cyclopropylaminoacrylate (48.1 g).

REFERENCE EXAMPLE 26

A mixture comprising ethyl 2-(4,6-dibromo-3-fluoro-2-methylbenzoyl)-3-cyclopropylaminoacrylate (45.0 g), potassium carbonate (16.7 g) and dimethylformamide (450 ml) is reacted at 140° C. for 30 minutes. After cooling, the reaction mixture is poured into ice-water and the precipitated crystals are filtered, which are recrystallized from ethanol to give ethyl 1-cyclopropyl-6-fluoro-7-bromo-5-methyl-1,4-dihydro-4-oxoquinoline-3-carboxylate (33.6 g), as white crystals, m.p. 195°–197° C.

REFERENCE EXAMPLE 27

Employing ethyl 1-cyclopropyl-6-fluoro-7-bromo-5-methyl-1,4-dihydro-4-oxoquinoline-3-carboxylate (32.5 g), the procedure of Reference Example 10 is repeated to give 1-cyclopropyl-6-fluoro-7-bromo-5-methyl-1,4-dihydro-4-oxoquinoline-3-carboxylic acid (27.2 g), as white crystals, m.p. 237°–239° C.

REFERENCE EXAMPLE 28

To 1-cyclopropyl-6-fluoro-7-bromo-5-methyl-1,4-dihydro-4-oxoquinoline-3-carboxylic acid (0.2 g) is added thionyl chloride (2 ml) and the mixture is refluxed for 1 hour. After cooling, the reaction mixture is poured into ice-water and made alkaline with 10% aqueous sodium hydroxide solution. After stirring for 30 minutes, the resultant is extracted with dichloromethane. The aqueous layer is made acidic with 10% hydrochloric acid and then extracted with dichloroethane. The solvent is concentrated and the residue is recrystallized from acetic acid to give 1-cyclopropyl-6-fluoro-7-chloro-5-methyl-1,4-dihydro-4-oxoquinoline-3-carboxylic acid (80 mg), as white crystals, m.p. 258°–260° C.

REFERENCE EXAMPLE 29

Employing ethyl 2-(2-methyl-3,4,6-trifluorobenzoyl)-3-ethoxyacrylate (1.0 g) and 2,4-difluoroaniline (0.5 g), the procedure of Reference Example 8 is repeated to give ethyl 2-(2-methyl-3,4,6-trifluorobenzoyl)-3-(2,4-difluorophenyl)aminoacrylate (1.1 g).

$^1$H-NMR (CDCl$_3$) δ ppm: 0.95 (3H, t, J=7.2 Hz), 2.23 (3H, d, J=2.4 Hz), 4.06 (2H, q, J=7.2 Hz), 6.70–6.83 (1H, m), 6.91–7.03 (2H, m), 7.26–7.45 (1H, m), 8.60 (1H, d, J=13.8 Hz), 11.36 (1H, d, J=13.8 Hz)

REFERENCE EXAMPLE 30

Employing ethyl 2-(2-methyl-3,4,6-trifluorobenzoyl)-3-(2,4-difluorophenyl)aminoacrylate (1.1 g) and 60% sodium hydride (0.13 g), the procedure of Reference Example 9 is repeated to give ethyl 1-(2,4-difluorophenyl)-5-methyl-6,7-difluoro-1,4-dihydro-4-oxoquinoline-3-carboxylate (0.7 g).

$^1$H-NMR (CDCl$_3$) δ ppm: 1.38 (3H, t, J=7.1 Hz), 2.91 (3H, d, J=3 Hz), 4.38 (2H, q, J=7.1 Hz), 6.46 (1H, dd, J=6.9 Hz, 11.1 Hz), 7.10–7.26 (2H, m), 7.38–7.56 (1H, m), 8.26 (1H, s)

REFERENCE EXAMPLE 31

Employing ethyl 1-(2,4-difluorophenyl)-5-methyl-6,7-difluoro-1,4-dihydro-4-oxoquinoline-3-carboxylate (0.7 g), the procedure of Reference Example 10 is repeated to give 1-(2,4-difluorophenyl)-5-methyl-6,7-difluoro-1,4-dihydro-4-oxoquinoline-3-carboxylic acid (0.5 g), colorless needles (recrystalized from acetic acid), m.p. 280°–281° C.

Example 1

To 3-(1-piperazinyl)-4-fluoro-5-methyl-6-nitro-N-cyclopropylaniline (1.57 g) is added diethyl ethoxymethylenemalonate (1.45 ml) and the mixture is heated at 150° C. for 25 hours. After cooling, the reaction product is purified by silica-gel column-chromatography (dichloromethane:methanol=100:1) to give diethyl [N-cyclopropyl-N-[3-(1-piperazinyl)-4-fluoro-5-methyl-6-nitrophenyl]amino-methylene]malonate (1.50 g). The product is dissolved in acetic anhydride (7.9 ml) and thereto conc. sulfuric acid (3.16 ml) is added dropwise at 50°–60° C., followed by stirring for 30 minutes. The resultant mixture is poured into ice-water, neutralized, extracted with dichloromethane and the extract is dried. The solvent is distilled off under reduced pressure. Purification by silica-gel column-chromatography (dichloromethane:methanol=10:1) to give ethyl 7-(1-piperazinyl)-1-cyclopropyl-6-fluoro-5-methyl-1,4-dihydro-4-oxoquinoline-3-carboxylate (26 mg).

Example 2

To ethyl 7-(1-piperazinyl)-1-cyclopropyl-6-fluoro-5-methyl-1,4-dihydro-4-oxoquinoline-3-carboxylate (23 mg) are added 10% aqueous solution of sodium hydroxide (3 ml) and ethanol (3 ml), and the mixture is refluxed for 1 hour. After cooling, the reaction mixture is diluted with water and washed with dichloromethane. After the aqueous layer is made acidic with acetic acid and then made weak alkaline with an aqueous sodium hydrogen carbonate. The resultant is extracted with dichloromethane and the extract is dried. The solvent is distilled off under reduced pressure and to the residue is added ethanol. The precipitated crystals are filtered and recrystallized from dimethylformamide to give 7-(1-piperazinyl)-1-cyclopropyl-6-fluoro-5-methyl-1,4-dihydro-4-oxoquinoline-3-carboxylic acid (12 mg), as white powder, m.p. 231°–233° C.

Example 3

To 6,7-difluoro-1-cyclopropyl-5-methyl-1,4-difluoro-4-oxoquinoline-3-carboxylic acid -B(OCOCH$_3$)$_2$ chelate (1.20 g) are added anhydrous 1-piperazine (0.86 g) and dimethylacetamide (6 ml), and the mixture is reacted at 50° C. for 20 hours. After concentrating, the obtained residue is dissolved in acetone (20 ml) and thereto conc. hydrochloric acid (5 ml) is added, followed by stirring at room temperature for 30 minutes. The solvent is distilled off and the resultant is added with water and extracted with dichloromethane. The aqueous layer is neutralized with an aqueous sodium hydrogen carbonate and extracted with dichloromethane. After drying over magnesium sulfate, the residue is added with ethanol. The precipitated crystals are filtered and recrystallized from dimethylformamide to give 7-(1-piperazinyl)-1-cyclopropyl-6-fluoro-5-methyl-1,4-dihydro-4-oxoquinoline-3-carboxylic acid (96 mg), as white powder, m.p. 231°–233° C.

Example 4

To a suspension of 6,7-difluoro-1-cyclopropyl-5-methyl-1,4-dihydro-4-oxoquinoline-3-carboxylic acid (0.15 g) in dimethylformamide (3 ml) is added anhydrous 1-piperazine (0.23 g) and the mixture is stirred at 90° C. for 30 minutes. After the reaction is completed, the reaction mixture is concentrated, and to the obtained residue is added ethanol. The precipitated crystals are filtered and recrystallized from dimethylformamide to give 7-(1-piperazinyl)-1-cyclopropyl-6-fluoro-5-methyl-1,4-dihydro-4-oxoquinoline-3-carboxylic acid (0.1 g), as white powder, m.p. 231°–233° C.

Example 5

Starting from suitable materials, the procedure of the above Examples 1–4 is repeated to give the following compounds.

1) 7-(4-Methyl-1-piperazinyl)-1-cyclopropyl-6-fluoro-5-methyl-1,4-dihydro-4-oxoquinoline-3-carboxylic acid, m.p. 229°–232° C., pale yellow prisms (recrystallized from ethanol)

2) 7-(3-Methyl-1-piperazinyl)-1-cyclopropyl-6-fluoro-5-methyl-1,4-dihydro-4-oxoquinoline-3-carboxylic acid, m.p. 206°–208° C., white powder (recrystallized from ethyl acetate-ethanol)

3) 7-(3-Amino-1-pyrrolidinyl)-1-cyclopropyl-6-fluoro-5-methyl-1,4-dihydro-4-oxoquinoline-3-carboxylic acid, m.p. 267°–270° C., white powder (recrystallized from dimethylformamide)

4) 7-Morpholino-1-cyclopropyl-6-fluoro-5-methyl-1,4-dihydro-4-oxoquinoline-3-carboxylic acid, m.p. 245°–247° C., white powder (recrystallized from ethanol)

5) 7-(3-Amino-4-methyl-1-pyrrolidinyl)-1-cyclopropyl-6-fluoro-5-methyl-1,4-dihydro-4-oxoquinoline-3-carboxylic acid hydrochloride (trans form), m.p. 272°–275° C. (dec.) white powder (recrystallized from methanol-ethyl acetate)

6) 7-(3-Aminomethyl-1-pyrrolidinyl)-1-cyclopropyl-6-fluoro-5-methyl-1,4-dihydro-4-oxoquinoline-3-carboxylic acid hydrochloride, m.p. 280°–283° C. (dec.), white powder (recrystallized from methanol-water)

7) 7-(4-Hydroxy-1-piperidinyl)-1-cyclopropyl-6-fluoro-5-methyl-1,4-dihydro-4-oxoquinoline-3-carboxylic acid, m.p. 220–°221° C., colorless needles (recrystallized from methanol)

8) 7-(4-Fluoro-1-piperidinyl)-1-cyclopropyl-6-fluoro-5-methyl-1,4-dihydro-4-oxoquinoline-3-carboxylic acid, m.p. 204–°207° C., white powder (recrystallized from ethanol)

9) 7-[3-(N-t-Butoxycarbonyl-N-methylamino)-1-pyrrolidinyl]-1-cyclopropyl-6-fluoro-5-methyl-1,4-dihydro-4-oxoquinoline-3-carboxylic acid, m.p. 210°–212° C., white powder (recrystallized from ethanol)

10) 7-(3-t-Butoxycarbonylamino-4-methyl-1-pyrrolidinyl)-1-cyclopropyl-6-fluoro-5-methyl-1,4-dihydro-4-oxoquinoline-3-carboxylic acid (cis form), m.p. 239°–241° C., white powder (recrystallized from ethanol)

11) 7-[3-(N-t-Butoxycarbonyl-N-ethylaminomethyl)-1-pyrrolidinyl]-1-cyclopropyl-6-fluoro-5-methyl-1,4-dihydro-4-oxoquinoline-3-carboxylic acid, m.p. 175°–177° C., white powder (recrystallized from ethanol)

12) 7-(3-Amino-4-methyl-1-pyrrolidinyl)-1-cyclopropyl-6propyl-6-fluoro-5-methyl-1,4-dihydro-4-oxoquinoline-3-carboxylic acid hydrochloride (cis form), m.p. 280°–284° C. (dec.), pale yellow powder (recrystallized from ethanol)

13) 7-(3-Ethylaminomethyl-1-pyrrolidinyl)-1-cyclopropyl-6-fluoro-5-methyl-1,4-dihydro-4-oxoquinoline-3-carboxylic acid hydrochloride, m.p. 236°–239° C., pale yellow powder (recrystallized from ethanol)

14) 7-(1,4-Diazabicyclo[4,3,0]nonan-4-yl)-1-cyclopropyl-6-fluoro-5-methyl-1,4-dihydro-4-oxoquinoline-3-carboxylic acid, m.p. 203°–205° C., colorless needles (recrystallized from ethanol)

15) 7-(4-Acetyl-1-piperazinyl)-1-cyclopropyl-6-fluoro-5-methyl-1,4-dihydro-4-oxoquinoline-3-carboxylic acid, m.p. 261°–263° C., white powder (recrystallized from ethanol)

16) 7-(3-Methylamino-1-pyrrolidinyl)-1-cyclopropyl-6-fluoro-5-methyl-1,4-dihydro-4-oxoquinoline-3-carboxylic acid, m.p. 194°–197° C., white powder (recrystallized from dimethylformamide)

17) 7-(3-t-Butoxycarbonylamino-4-methyl-1-pyrrolidinyl)-1-cyclopropyl-6-fluoro-5-methyl-1,4-dihydro-4-oxoquinoline-3-carboxylic acid (trans form), m.p. 226°–229° C., white powder (recrystallized from ethanol)

18) 7-[4-(5-Methyl-2-oxo-1,3-dioxolen-4-yl)methyl-1-piperazinyl]-1-cyclopropyl-6-fluoro-5-methyl-1,4-dihydro-4-oxoquinoline-3-carboxylic acid $^1$H-NMR (CDCl$_3$) δ ppm: 1.14–1.24 (2H, m), 1.26–1.41 (2H, m), 2.16 (3H, s), 2.72–2.84 (7H, m), 3.28–3.53 (7H, m), 7.29 (1H, d, 8.2 Hz), 8.7.3 (1H, s), 15.57 (1H, s)

19) 7-(1-Piperazinyl)-1-(4-fluorophenyl)-6-fluoro-5-methyl-1,4-dihydro-4-oxoquinoline-3-carboxylic acid, m.p. 278°–282° C. (dec.), yellowish crystals (recrystallized from dimethylformamide)

20) 7-(3-t-Butoxycarobonylamino-1-pyrrolidinyl)-1-(4-fluorophenyl)-6-fluoro-5-methyl-1,4-dihydro-4-oxoquinoline-3-carboxylic acid, m.p. 249°–250° C., white crystals (recrystallized from ethanol)

21) 7-(3-Amino-1-pyrrolidinyl)-1-(4-fluorophenyl)-6-fluoro-5-methyl-1,4-dihydro-4-oxoquinoline-3-carboxylic acid hydrochloride, m.p. 292°–295° C. (dec.), pale yellowish white crystals (recrystallized from methanol-water)

22) 7-(1-Piperazinyl)-1-ethyl-6-fluoro-5-methyl-1,4-dihydro-4-oxoquinoline-3-carboxylic acid, m.p. 225°–227° C., white crystals (recrystallized from dimethylformamide)

23) 7-(3-t-Butoxycarbonylamino-1-pyrrolidiny)-1-ethyl-6-fluoro-5-methyl-1,4-dihydro-4-oxoquinoline-3-carboxylic acid, m.p. 230°–231° C., white crystals (recrystallized from ethanol)

24) 7-(3-Amino-1-pyrrolidinyl)-1-ethyl-6-fluoro-5-methyl-1,4-dihydro-4-oxoquinoline-3-carboxylic acid hydrochloride, m.p. 275°–281° C. (dec.), yellowish crystals (recrystallized from ethanol)

25) 7-(4-Methyl-1-piperazinyl)-1-(4-fluorophenyl)-6-fluoro-5-methyl-1,4-dihydro-4-oxoquinoline-3-carboxylic acid, m.p. 274°–276° C. (dec.), white crystals (recrystallized from ethanol)

26) 7-(4-Methyl-1-piperazinyl)-1-(2,4-difluorophenyl)-6-fluoro-5-methyl-1,4-dihydro-4-oxoquinoline-3-carboxylic acid, m.p. 226°–228° C., pale yellow crystals (recrystallized from ethanol)

27) 7-(1-Piperazinyl)-1-(2,4-difluorophenyl)-6-fluoro-5-methyl-1,4-dihydro-4-oxoquinoline-3-carboxylic acid hydrochloride, m.p. 229°–232° C., white crystals (recrystallized from ethanol-water)

28) 7-(3-Amino-1-pyrrolidinyl)-1-(2,4-difluorophenyl)-6-fluoro-5-methyl-1,4-dihydro-4-oxoquinoline-3-carboxylic acid hydrochloride, m.p. 291°–294° C., white crystals (recrystallized from ethanol-water)

Example 6

A mixture comprising 7-(3-t-butoxycarbonylamino-4-methyl-1-pyrrolidinyl)-1-cyclopropyl-6-fluoro-5-methyl-1,4-dihydro-4-oxoquinoline-3-carboxylic acid (trans form) (120 mg), ethanol (4 ml) and 10% hydrochloric acid (4 ml) is refluxed for 30 minutes. After concentrating, the obtained residue is recrystallized from methanol-ethyl acetate to give 7-(3-amino-4-methyl-1-pyrrolidinyl)-1-cyclopropyl-6-fluoro-5-methyl-1,4-dihydro-4-oxoquinoline-3-carboxylic acid hydrochloride (trans form) (60 mg), as white powder, m.p. 272°–275° C.

Starting from suitable materials, the procedure of Example 6 is repeated to give the following compounds.

1) 7-(3-Amino-4-methyl-1-pyrrolidinyl)-1-cyclopropyl-6-fluoro-5-methyl-1,4-dihydro-4-oxoquinoline-3-carboxylic acid hydrochloride (cis form), m.p. 280°–284° C. (dec.), pale yellow powder (recrystallized from ethanol)

2) 7-(3-Ethylaminomethyl-1-pyrrolidinyl)-1-cyclopropyl-6-fluoro-5-methyl-1,4-dihydro-4-oxoquinoline-3-carboxylic acid hydrochloride, m.p. 236°–239° C., pale yellow powder (recrystallized from ethanol)

3) 7-(3-Methylamino-1-pyrrolidinyl)-1-cyclopropyl-6-fluoro-5-methyl-1,4-dihydro-4-oxoquinoline-3-carboxylic acid, m.p. 194°–197° C., white powder (recrystallized from dimethylformamide)

4) 7-(3-Amino-1-pyrrolidinyl)-1-(4-fluorophenyl)-6-fluoro-5-methyl-1,4-dihydro-4-oxoquinoline-3-carboxylic acid hydrochloride, m.p. 292°–295° C. (dec.), pale yellow crystals (recrystallized-from methanol-water)

5) 7-(3-Amino-1-pyrrolidinyl)-1-ethyl-6-fluoro-5-methyl-1,4-dihydro-4-oxoquinoline-3-carboxylic acid hydrochloride, m.p. 275°–281° C. (dec.), yellowish crystals (recrystallized from ethanol)

Example 7

To a solution of 7-(1-piperazinyl)-1-cyclopropyl-6-fluoro-5-methyl-1,4-dihydro-4-oxoquinoline-3-carboxylic acid (40 mg) in 5% sodium hydroxide (2 ml) is added acetic anhydride (0.1 ml) at room temperature. After the mixture is made acidic with dilute hydrochloric acid, the resultant is extracted with dichloromethane and the extract is dried over magnesium sulfate. After concentrating, the obtained residue is recrystallized from ethanol to give 7-(4-acetyl-1-piperazinyl)-1-cyclopropyl-6-fluoro-5-methyl-1,4-dihydro-4-oxoquinoline-3-carboxylic acid (29 mg), as white powder, m.p. 261°–263° C.

Example 8

To a solution of 1-cyclopropyl-6-fluoro-7-bromo-5-methyl-1,4-dihydro-4-oxoquinoline-3-carboxylic acid (0.58 g) in N-methyl-2-pyrrolidone (5 ml) is added 4-oxopiperidine (0.64 g) and the mixture is heated at 90° C. for 20 minutes. The solvent is distilled off under reduced pressure. To the resulting residue is added ethanol and the precipitated crystals are filtered to give 1-cyclopropyl-6-fluoro-7-(4-oxo-1-piperidinyl)-5-methyl-1,4-dihydro-4-oxoquinoline-3-carboxylic acid (230 mg).

Elementary Analysis for $C_{19}H_{19}N_2O_4F$ Calcd. (%): C, 63.68; H, 5.34; N, 7.82 Found (%): C, 63.58; H, 5.39; N, 7.72

Experiment (Antimicrobial activity in vitro)

The antimicrobial activity of the test compounds as mentioned below was tested by measuring minimum inhibitory concentration (MIC) by the serial dilution method on agar plate [cf. Chemotherapy, 22, 1126–1128 (1974)]. The microorganisms were used in a concentration of $1\times10^6$ cells/ml (O.D. 660 mμ, 0.07–0.16, 100 folds dilution). The results are shown in Table 1.

[Test compounds]

1. 7-(4-Methyl-1-piperazinyl)-1-cyclopropyl-6-fluoro-5-methyl-1,4-dihydro-4-oxoquinoline-3-carboxylic acid
2. 7-(1-Piperazinyl)-1-cyclopropyl-6-fluoro-5-methyl-1,4-dihydro-4-oxoquinoline-3-carboxylic acid
3. 7-(3-Amino-1-pyrrolidinyl)-1-cyclopropyl-6-fluoro-5-methyl-1,4-dihydro-4-oxoquinoline-3-carboxylic acid
4. 7-(3-Methyl-1-piperazinyl)-1-cyclopropyl-6-fluoro-5-methyl-1,4-dihydro-4-oxoquinoline-3-carboxylic acid
5. 7-(3-Aminomethyl-1-pyrrolidinyl)-1-cyclopropyl-6-fluoro-5-methyl-1,4-dihydro-4-oxoquinoline-3-carboxylic acid hydrochloride
6. 7-(3-Amino-4-methyl-1-pyrrolidinyl)-1-cyclopropyl-6-fluoro-5-methyl-1,4-dihydro-4-oxoquinoline-3-carboxylic acid hydrochloride (trans form)
7. 7-Morpholino-1-cyclopropyl-6-fluoro-5-methyl-1,4-dihydro-4-oxoquinoline-3-carboxylic acid
8. 7-(3-Ethylaminomethyl-1-pyrrolidinyl)-1-cyclopropyl-6-fluoro-5-methyl-1,4-dihydro-4-oxoquinoline-3-carboxylic acid hydrochloride
9. 7-(1,4-Diazabicyclo[4,3,0]nonan-4-yl)-1-cyclopropyl-6-fluoro-5-methyl-1,4-dihydro-4-oxoquinoline-3-carboxylic acid
10. 7-(4-Hydroxy-1-piperidinyl)-1-cyclopropyl-6-fluoro-5-methyl-1,4-dihydro-4-oxoquinoline-3-carboxylic acid
11. 7-(4-Fluoro-1-piperidinyl)-1-cyclopropyl-6-fluoro-5-methyl-1,4-dihydro-4-oxoquinoline-3-carboxylic acid
12. 7-(3-Amino/4-methyl-1-pyrrolidinyl)-1-cyclopropyl-6-fluoro-5-methyl-1,4-dihydro-4-oxoquinoline-3-carboxylic acid (cis form)
13. 7-(4-Acetyl-1-piperazinyl)-1-cyclopropyl-6-fluoro-5-methyl-1,4-dihydro-4-oxoquinoline-3-carboxylic acid
14. 7-(3-Methylamino-1-pyrrolidinyl)-1-cyclopropyl-6-fluoro-5-methyl-1,4-dihydro-4-oxoquinoline-3-carboxylic acid
15. 7-(1-Piperazinyl)-1-(4-fluorophenyl)-6-fluoro-5-methyl-1,4-dihydro-4-oxoquinoline-3-carboxylic acid
16. 7-(3-Amino-1-pyrrolidinyl)-1-(4-fluorophenyl)-6-fluoro-5-methyl-1,4-dihydro-4-oxoquinoline-3-carboxylic acid hydrochloride
17. 7-(4-Methyl-1-piperazinyl)-1-(4-fluorophenyl)-6-fluoro-5-methyl-1,4-dihydro-4-oxoquinoline-3-carboxylic acid
18. 7-(4-Methyl-1-piperazinyl)-1-(2,4-difluorophenyl)-6-fluoro-5-methyl-1,4-dihydro-4-oxoquinoline-3-carboxylic acid
19. 7-(1-Piperazinyl)-1-(2,4-difluorophenyl)-6-fluoro-5-methyl-1,4-dihydro-4-oxoquinoline-3-carboxylic acid hydrochloride 20. 7-(3-Amino-1-pyrrolidinyl)-1-(2,4-difluorophenyl)-6-fluoro-5-methyl-1,4-dihydro-4-oxoquinoline-3-carboxylic acid hydrochloride

[Test microorganisms]

A: *Staphylococcus aureus* FDA 209P
B: *Staphylococcus aeruginosa* E-2

TABLE 1

| Test compounds | Microorganisms A | B |
|---|---|---|
| 1 | 0.195 | 0.78 |
| 2 | 0.098 | 0.39 |
| 3 | 0.098 | 0.39 |
| 4 | 0.098 | 0.39 |
| 5 | 0.098 | 1.56 |
| 6 | 0.195 | 0.78 |
| 7 | 0.098 | — |
| 8 | 0.195 | — |
| 9 | 0.049 | 0.78 |
| 10 | 0.049 | — |
| 11 | 0.098 | — |
| 12 | 0.195 | 0.78 |
| 13 | 0.098 | — |
| 14 | 0.098 | 0.78 |
| 15 | 0.049 | 0.39 |
| 16 | 0.098 | 0.39 |
| 17 | 0.195 | 1.56 |
| 18 | 0.098 | 1.56 |
| 19 | 0.098 | 0.39 |
| 20 | 0.024 | 0.78 |

Preparation 1

An injection preparation is prepared from the following components.

| Components | Amount |
|---|---|
| 7-(1-Piperazinyl)-1-cyclopropyl-6-fluoro-5-methyl-1,4-dihydro-4-oxo-quinoline-3-carboxylic acid | 200 mg |
| Glucose | 250 mg |
| Distilled water for injection | q.s. |
| Totally | 5 ml |

7-(1-Piperazinyl)-1-cyclopropyl-6-fluoro-5-methyl-1,4-dihydro-4-oxoquinoline-3-carboxylic acid and glucose are dissolved in distilled water for injection, and the solution is added to a 5 ml ampoule, which is purged with nitrogen gas and then subjected to sterilization at 121° C. for 15 minutes to give an injection preparation.

Preparation 2

Film coated tablets are prepared from the following components.

| Components | Amount |
|---|---|
| 7-(3-Methyl-1-piperazinyl)-1-cyclopropyl-6-fluoro-5-methyl-1,4-dihydro-4-oxoquinoline-3-carboxylic acid | 100 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| TC-5 (tradename of hydroxypropyl methylcellulose, | 10 g |

-continued

| Components | Amount |
|---|---|
| manufactured by The Shin-Etsu Chemical Co., Ltd., Japan) | |
| Polyethylene glycol 6000 | 3 g |
| Castor oil | 40 g |
| Ethanol | 40 g |

7-(3-Methyl-1-piperazinyl)-1-cyclopropyl-6-fluoro-5-methyl-1,4-dihydro-4-oxoquinoline-3-carboxylic acid, Avicel, corn starch and magnesium stearate are mixed and kneaded and the mixture is tabletted using a conventional pounder (R 10 mm) for sugar coating (manufactured by Kikusui Seisakusho Co., Ltd., Japan). The tablets thus obtained are coated with a film coating agent consisting of TC-5, polyethylene glycol 6000, castor oil and ethanol to give film coated tablets.

Preparation 3

An ointment is prepared from the following components.

| Components | Amount |
|---|---|
| 7-(4-Methyl-1-piperazinyl)-1-cyclopropyl-6-fluoro-5-methyl-1,4-dihydro-4-oxo-quioline-3-carboxylic acid | 2 g |
| Purified lanolin | 5 g |
| Bleached beeswax | 5 g |
| White vaseline | 88 g |
| Totally | 100 g |

Bleached beeswax is made liquid by heating, and thereto are added 7-(4-methyl-1-piperazinyl)-1-cyclopropyl-6-fluoro-5-methyl-1,4-dihydro-4-oxoquinoline-3-carboxylic acid, purified lanolin and while vaseline, and the mixture is heated until it becomes liquid. The mixture is stirred until it is solidified to give an ointment.

What is claimed is:

1. A compound of the formula:

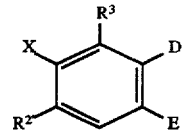

wherein X is a halogen atom,
$R^3$ is a lower alkyl group; $R^{2'}$ is a halogen atom or a 5- to 9-membered saturated or unsaturated heterocyclic group that may be substituted; E is a halogen atom; and
D is a group of the formula:

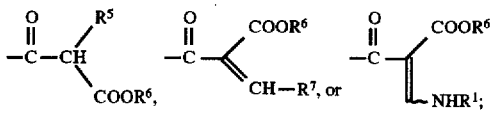

wherein $R^5$ is a group of the formula: —$COR^{10}$ ($R^{10}$ is a lower alkyl group) or a group of the formula: —$COOR^{11}$ ($R^{11}$ is a lower alkyl group), $R^6$ is a lower alkyl group, $R^7$ is a group of the formula: —$NR^{12}R^{13}$ ($R^{12}$ and $R^{13}$ are each a lower alkyl group) or a lower alkoxy group, $R^1$ is a cyclopropyl group that may be substituted by 1 to 3 of substituents selected from the group consisting of a lower alkyl group and a halogen atom, a phenyl group that may be substituted by 1 to 3 of substituents selected from the group consisting of a lower alkoxy group, a halogen atom and a hydroxy group, a lower alkyl group that may be substituted by a halogen atom, a lower alkanoyloxy group or a hydroxy group, a lower alkenyl group, or a thienyl group.

2. A compound according to claim 1, which is a member selected from the group consisting of diethyl 2-methyl-3,4,6-trifluorobenzoylmalonate;

ethyl 2-(2-methyl-3,4,6-trifluorobenzoyl)-3-ethoxyacrylate;

ethyl 2-(2-methyl-3,4,6-trifluorobenzoyl)-3-cyclopropylaminoacrylate;

diethyl 4,6-dibromo-3-fluoro-2-methylbenzoylmalonate;

ethyl 2-(4,6-dibromo-3-fluoro-2-methylbenzoyl)-3-ethoxyacrylate;

ethyl 2-(4,6-dibromo-3-fluoro-2-methylbenzoyl)-3-cyclopropyl-aminoacrylate; and ethyl 2-(2-methyl-3,4,6-trifluorobenzoyl)-3-(2,4-difluorophenyl)-aminoacrylate.

3. The compound according to claim 1, which is diethyl 4,6-dibromo-3-fluoro-2-methylbenzoylmalonate.

4. The compound according to claim 1, which is ethyl 2-(4,6-dibromo-3-fluoro-2-methylbenzoyl)-3-ethoxyacrylate.

5. The compound according to claim 1, which is ethyl 2-(4,6-dibromo-3-fluoro-2-methylbenzoyl)-3-cyclopropylaminoacrylate.

* * * * *